(12) United States Patent
Mahashabde et al.

(10) Patent No.: US 6,264,973 B1
(45) Date of Patent: Jul. 24, 2001

(54) APPARATUS AND METHOD FOR ANESTHETIZING THE CERVICAL REGION OF A FEMALE

(75) Inventors: Anu Mahashabde, Kendall Park; Martha Francine Kay, Lawrenceville, both of NJ (US); Louis J. Mestichelli, Doylestown, PA (US); Ann Elizabeth Gooding, Hopewell; Suzanne Wilford Ruth, Hillsborough, both of NJ (US)

(73) Assignee: FEI Enterprises, Ltd., North Tonawanda, NY (US)

( * ) Notice: Subject to any disclaimer, the term of this patent is extended or adjusted under 35 U.S.C. 154(b) by 0 days.

(21) Appl. No.: 09/383,887

(22) Filed: Aug. 26, 1999

(51) Int. Cl.$^7$ .............. A61F 6/14; A61F 13/02; A61F 6/06
(52) U.S. Cl. ............ 424/432; 424/430; 424/431
(58) Field of Search .............. 424/430, 431, 424/432; 514/772.3

(56) References Cited

U.S. PATENT DOCUMENTS

| 4,478,822 | 10/1984 | Haslem et al. . |
| 5,474,783 | 12/1995 | Miranda et al. . |
| 5,622,993 | 4/1997 | McGinty et al. . |
| 5,635,159 | 6/1997 | Fu Lu et al. . |
| 5,776,952 | 7/1998 | Liedtke . |
| 5,922,340 | 7/1999 | Berde et al. . |
| 6,086,909 | * 7/2000 | Harrison et al. ............ 424/430 |

FOREIGN PATENT DOCUMENTS

| 0335545B1 | 10/1989 | (EP) . |
| 0573576B1 | 12/1993 | (EP) . |

* cited by examiner

Primary Examiner—Carlos A. Azpuru
(74) Attorney, Agent, or Firm—Gibbons, Del Deo, Dolan, Griffinger & Vecchione

(57) ABSTRACT

A novel and useful apparatus for delivering an anesthetic locally to the cervical region of a female is provided, wherein the apparatus comprises a ring having a surface and at least one depression on the surface. An anesthetic composition comprising an anesthetic agent and an excipient are placed within the at least one depression. The ring is comprised of a pharmaceutically acceptable inert material that is biocompatible. Furthermore, the ring is of sufficient size such that it can be inserted into the vaginal canal of a female. In the vaginal canal, the anesthetic agent is immediately released from the anesthetic composition and directly anesthetizes the cervical region.

47 Claims, 13 Drawing Sheets

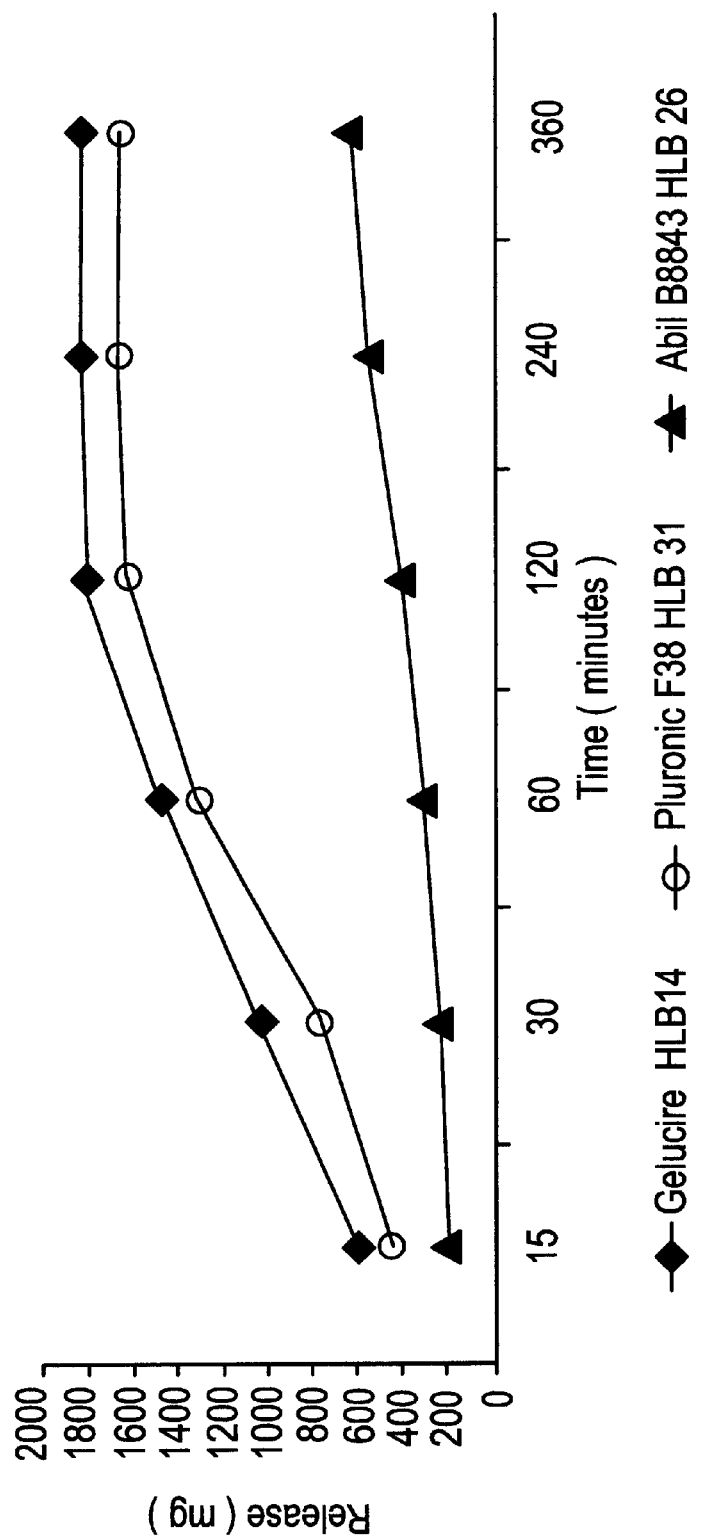

FIG. 5A
FIG. 5B
FIG. 5C
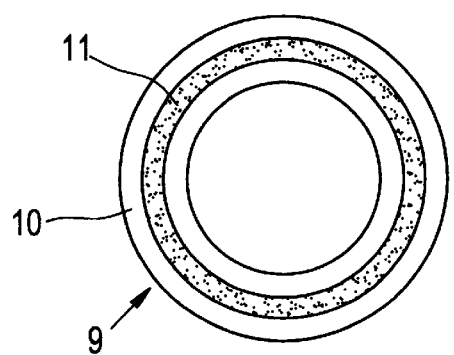
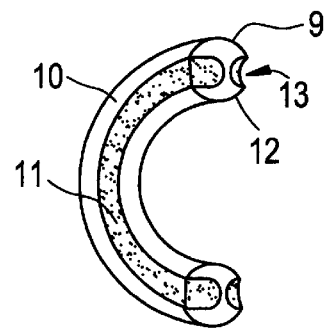
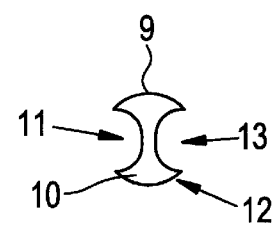

FIG. 9A
FIG. 9B
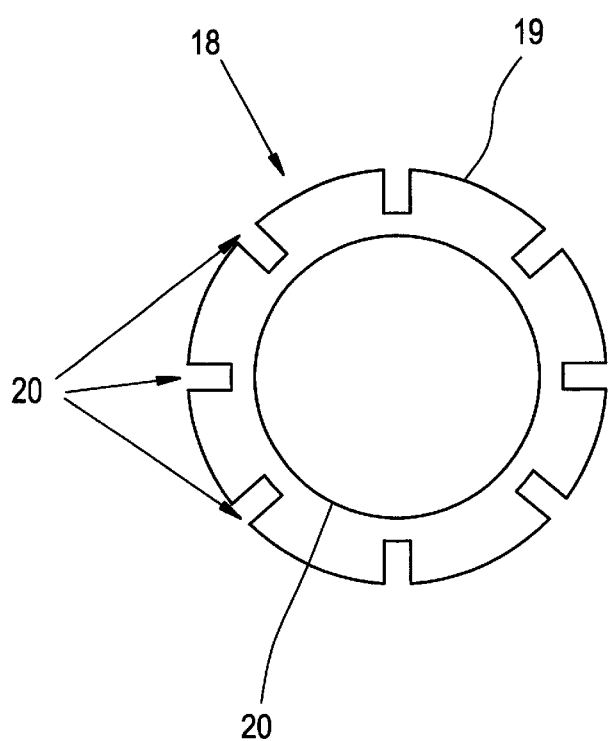
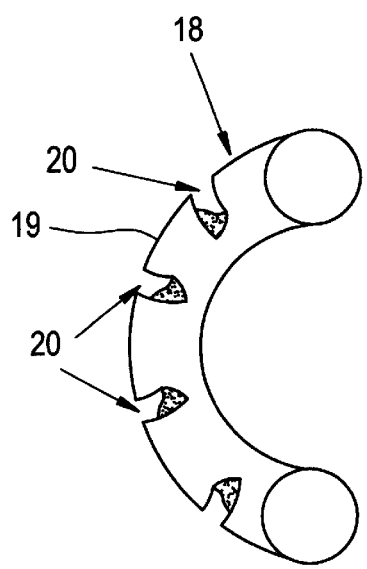

APPARATUS AND METHOD FOR ANESTHETIZING THE CERVICAL REGION OF A FEMALE

FIELD OF THE INVENTION

The present invention relates to a novel apparatus for locally delivering and immediately releasing an anesthetic agent to the cervical region of a female such that the cervical region is temporarily anesthetized in anticipation of the performance of a gynecological procedure on the female.

BACKGROUND OF THE INVENTION

Many gynecological procedures, such as endometrial and cervical sampling, the Loop Electrosurgial Excision Procedure (LEEP), endometrial biopsies, hysteroscopies, dilation and curettage, and laser conization to name only a few, are being performed more frequently on an out-patient basis than in a hospital setting. Since such procedures can be painful, it is desirable that the cervical region, which includes the upper portion of the vagina and the lower portion of the uterus, be locally anesthetized prior to commencement of the procedure. Thus, methods have been developed for temporarily anesthetizing the cervical region. One such method involves an epidural injection of an anesthetic agent, or the insertion of an epidural catheter into the female. However, this method requires an injection or perforation of the epidural matter of the spine, and thus inherently inflicts pain and discomfort on the female. Moreover, it is labor intensive, time consuming, expensive, and technically difficult to perform.

Another method for locally anesthetizing the cervical region is the direct injection of an anesthetic agent into the cervical region of the female paracervical block. However, just as with an epidural injection, this method can also cause pain and discomfort to the female being anesthetized. Furthermore, this method requires the treating medical provider to possess the requisite skills to make such an injection. Also, this method can result in one or a number of recognized complications.

Still another method for anesthetizing the cervical region involves the local application of an anesthetic agent to the vaginal mucosa of the cervical region. However, this method also possesses inherent limitations. For example, the anesthetic agent can diffuse from the local point or area to be anesthetized. Thus, the amount of anesthetic agent that must be applied to the area must compensate for such diffusion. As a result, the female is exposed to a greater amount of anesthetic agent than is actually needed to anesthetize the region.

Accordingly what is needed is an apparatus that delivers an anesthetic agent locally to the cervical region of the female, and immediately releases the anesthetic agent to the cervical region. As a result, the region can be temporarily anesthetized in anticipation of the performance of a gynecological procedure.

What is also needed is an apparatus and method for locally delivering an anesthetic agent to the cervical region of a female that is easy to use, and lends itself to use in an outpatient setting, such as a doctor's office. As a result, medical providers who do not possess the requisite training to deliver anesthetic agents with methods described above can readily use such an apparatus, and thus increase the number of females that can be locally anesthetized in an out-patient setting. Also, the time, expense and risk of complications associated with alternatives described above can be reduced.

The citation of any reference herein should not be construed as an admission that such reference is available as "Prior Art" to the instant application.

SUMMARY OF THE INVENTION

There is provided, in accordance with the invention, a new and useful apparatus and method for delivering an anesthetic agent locally to the cervical region in the female to induce anesthesia temporarily of the cervical region.

Broadly, the present invention extends to an apparatus for locally delivering and immediately releasing an anesthetic agent to the cervical region of a female, wherein the apparatus comprises a ring having a surface, and at least one depression on the surface. Moreover, the ring is comprised of a pharmaceutically acceptable inert material, and has a sufficient size such that it can be inserted into the vaginal canal of the female, and be retained therein temporarily. An apparatus of the invention also comprises an anesthetic composition which is located within the at least one depression, wherein the anesthetic composition comprises the anesthetic agent and an excipient. Upon the insertion of the ring into the vaginal canal, the anesthetic agent is immediately released from the anesthetic composition, and induces temporary anesthesia in the cervical region. As a result, a gynecological procedure can be performed on the female with the ring either in place in the cervical region or removed, and the pain and discomfort associated with the procedure can be avoided.

Furthermore, the ring of an apparatus of the invention comprises numerous pharmaceutically acceptable inert materials. Particular examples of such a pharmaceutically acceptable inert material include ethylene-vinyl acetate copolymer, polyethylene, polypropylene, polyvinyl chooride, cellulose derivatives, thermoplastic rubber, thermoplastic elastomer, polyurethane, and polydimethylsiloxane, to name only a few.

Moreover, the present invention extends to an apparatus as described above, for locally delivering and immediately releasing an anesthetic agent to the cervical region of a female, wherein, an anesthetic composition comprises approximately 60% by weight the anesthetic agent and approximately 40% by weight the excipient. Numerous anesthetic agents have applications in an apparatus of the invention. Moreover, anesthetic agents having applications herein can be in a free base form or an acid addition salt form, or a mixture thereof. Particular examples of anesthetic agents having applications herein include, but are not limited to, bupivacaine, ropivacaine, dibucaine, procaine, chloroprocaine, prilocaine, mepivacaine, etidocaine, tetracaine, lidocaine, benzocaine, or a mixture thereof.

Likewise, numerous excipients have applications in an apparatus of the invention. Examples of such excipients include a saturated polyglycolyzed glyceride, a block copolymer surfactant, an emulsifier, glyceryl monolaurate, silicone, e.g. condensation cured silicone elastomer, microcrystalline cellulose, hydroxyethylcellulose, ethylcellulose, hydroxypropyl methylcellulose, polymethylmethacrylate, polyvinylpyrollidone, or a mixture thereof, to name only a few.

Furthermore, the at least one depression on the surface of a ring of an apparatus of the invention, as described above, can have numerous sizes or shapes. For example, the at least one depression can comprise at least one notch on the surface of the ring. Naturally, the at least one notch can comprise a plurality of notches on the outer surface of the ring. In a particular embodiment, the plurality of notches comprises 8 notches.

In addition, the at least one depression can comprise at least one channel on the surface of the ring. The at least one channel can be located on the upper surface, the lower surface, the inner surface or the outer surface of the ring. In an embodiment of the invention, the at least one channel comprises a channel on either the upper or lower surface of the ring. In another embodiment, the at least one channel comprises a first channel on the lower surface of the ring, and a second channel on the upper surface of the ring. In yet another embodiment, the at least one channel comprises a channel on the outer surface of the ring.

Moreover, the at least one depression on a ring of an apparatus of the invention can comprise at least one bore through the ring. In a particular embodiment, the at least one bore in the ring comprises a plurality of bores through the ring, running from the upper surface to the lower surface.

Furthermore, the present invention extends to an apparatus for locally delivering and immediately releasing an anesthetic agent to the cervical region of a female to anesthetize the cervical region, wherein the apparatus comprises (a) a ring having an inner surface, an outer surface, a lower surface, an upper surface, and a channel on the outer surface, wherein the ring is comprised of a pharmaceutically acceptable inert material, and has a sufficient size such that it can be inserted into the vaginal canal of the female and retained therein temporarily, and (b) an anesthetic composition located within the channel, wherein the anesthetic composition comprises an anesthetic agent and an excipient. Upon insertion of the ring into the vaginal canal of a female, the anesthetic agent is immediately released from the anesthetic composition, and induces temporary anesthesia in the cervical region.

Numerous pharmaceutically acceptable inert materials have applications in an apparatus of the invention described above. Particular examples include, but certainly are not limited to ethylene-vinyl acetate copolymer, polyethylene, polypropylene, polyurethane, polyvinylchloride, cellulose derivatives, thermoplastic rubber, thermoplastic elastomer, or polydimethylsiloxane. Moreover, numerous anesthetic agents have applications herein. The anesthetic agent can be in a free base form or an acid addition salt form. Particular examples of such anesthetic agents include, but certainly are not limited to bupivacaine, ropivacaine, dibucaine, procaine, chloroprocaine, prilocaine, mepivacaine, etidocaine, tetracaine, lidocaine, benzocaine, or a mixture thereof. In a particular embodiment, the anesthetic composition comprises about 60% by weight the anesthetic agent, and about 40% by weight the excipient.

The present invention further extends to an apparatus for locally delivering and immediately releasing lidocaine to the cervical region of a female in order to anesthetize the cervical region, comprising (a) a ring having an inner surface, an outer surface, a lower surface, an upper surface, and a channel on the outer surface, wherein the ring is comprised of ethylene-vinyl acetate copolymer, and has a sufficient size such that it can be inserted into the vaginal canal of the female, and (b) an anesthetic composition located within the channel, wherein the anesthetic composition comprises about 60% by weight lidocaine and about 40% by weight an excipient comprising saturated polyglycolyzed glyceride. Upon insertion of the ring into the vaginal canal of the female, the lidocaine is immediately released from the anesthetic composition, and induces temporary anesthesia in the cervical region.

The present invention also extends to an apparatus for locally delivering and immediately releasing lidocaine to the cervical region of a female in order to anesthetize the cervical region, wherein the apparatus comprises a ring having a surface which comprises an upper surface, a lower surface, an inner surface and an outer surface, and a channel on the outer surface. The ring comprises a pharmaceutically acceptable inert material, and has a sufficient size such that it can be inserted into the vaginal canal of the female and retained therein temporarily. An anesthetic composition comprising 60% by weight lidocaine and about 40% by weight an excipient is located within the at least one channel. Upon insertion of the ring into the vaginal canal of the female, the lidocaine is immediately released from the anesthetic composition, and induces temporary anesthesia in the cervical region. The lidocaine can be in a free base form, an acid addition salt form, or a mixture thereof. Moreover, numerous excipients have applications in such an apparatus of the invention. Particular examples include a saturated polyglycolyzed glyceride, e.g., lauroyl macrogolglyceride or stearoyl macrogolglyceride, or a block copolymer surfactant.

In addition, the present invention extends to methods for locally delivering and immediately releasing an anesthetic agent to the cervical region of a female in order to anesthetize the cervical region. As a result, the cervical region is temporarily anesthetized for the performance of a gynecological procedure on the female. In particular, the present invention extends to a method for locally delivering and immediately releasing an anesthetic agent to the cervical region of a female in order to temporarily induce anesthesia in the cervical region, comprising providing a ring having a surface, and at least one depression on the surface, and an anesthetic composition comprising an anesthetic agent and an excipient, wherein the anesthetic agent is located within the at least one depression on the surface of the ring. The ring comprises a pharmaceutically acceptable inert material, and has a sufficient size such that it can be inserted into the vaginal canal of the female and retained therein temporarily. A method of the invention also comprises inserting the ring into the vaginal canal of the female, so that the anesthetic agent is immediately released from the anesthetic composition, contacts the female's vaginal mucosa, and induces temporary anesthesia in the female's cervical region. The ring can be removed from the vaginal canal prior to, or after the performance of a gynecological procedure.

Moreover, the present invention extends to a method for locally delivering and immediately releasing an anesthetic agent to the cervical region of a female, as described above, wherein the pharmaceutically acceptable inert material includes, but certainly is not limited to, ethylene-vinylacetate copolymer, polyethylene, polypropylene, polyurethane, polyvinylchloride, cellulose derivatives, thermoplastic rubber, thermoplastic elastomer elastomer, or polydimethylsiloxane. Also, the quantity of anesthetic agent and excipient in an anesthetic composition can vary, depending upon the particular application of such a method. In a particular embodiment, the anesthetic composition comprises about 60% by weight the anesthetic agent and about 40% by weight the excipient. Naturally, the anesthetic agent can be in a free base form, an acid addition salt form, or a mixture thereof. Particular examples of anesthetic agents having applications in a method of the invention include chloroprocaine, prilocaine, mepivacaine, etidocaine, tetracaine, lidocaine, benzocaine, or a mixture thereof, to name only a few. Also, numerous excipients have applications in a method of the invention, e.g., a saturated polyglycolyzed glyceride, a block copolymer surfactant, an emulsifier, glyceryl monolaurate, silicone (condensation cured silicone elastomer), microcrystalline cellulose, hydroxyethylcellulose, ethylcellulose, hydroxypropyl methylcellulose, polymethylmethacrylate, polyvinylpyrollidone, or a mixture thereof.

Moreover, the at least one depression on the surface of the ring can have numerous forms or shapes. For example, the at least one depression can comprise at least one notch on the surface of the ring. In a particular embodiment of a method of the invention, wherein the surface of the ring comprises an upper surface, a lower surface, an inner surface and an outer surface, the at least one notch comprises a plurality of notches on the outer surface.

Moreover, the at least one depression on a ring of a method of the invention can comprise at least one channel on the surface of the ring. Naturally, the surface of a ring of a method of the invention comprises an upper surface, a lower surface, an inner surface, and an outer surface. Thus, the at least one channel can be located on any of these surfaces. In a particular embodiment of a method of the invention, the at least one channel is located on the upper surface. In another embodiment, the at least one channel is located on the lower surface. Also, the at least one channel comprises a first channel and a second channel, wherein the first channel is located on the upper surface, and the second channel is located on the lower surface. In yet another embodiment, the at least one channel is located on the outer surface.

In addition, the at least one depression on a ring of a method of the invention can comprise at least one bore in the ring. The at least one bore can penetrate into the interior of the ring, or alternatively, pass through the ring. In a particular embodiment of a method of the invention, the at least one bore comprises a plurality of bores which pass through the ring and run from the upper surface to the lower surface.

Moreover, the present invention extends to a method for locally delivering and immediately delivering an anesthetic agent to the cervical region of a female to anesthetize the cervical region, comprising the steps of:

(a) providing a ring having an inner surface, an outer surface, a lower surface, an upper surface, and a channel on the outer surface, wherein the ring is comprised of ethylene-vinyl acetate copolymer, and has a sufficient size such that it can be inserted into the vaginal canal of the female and retained therein temporarily;

(b) providing an anesthetic composition located within the channel, wherein the anesthetic composition comprises the anesthetic agent and an excipient;

(c) inserting the ring into the vaginal canal of the female so that the anesthetic agent is immediately released from the anesthetic composition, and induces temporary anesthesia in the female's cervical region; and (d) removing the ring from the vaginal canal after induction of temporary anesthesia of the cervical region either prior to or after performance of a gynecological procedure.

The anesthetic composition of a method described above can comprise a varied amount of anesthetic agent and excipient, depending upon the application. Moreover, the anesthetic agent can be in a free base form, an acid addition salt form, or a mixture thereof. In a particular embodiment, the anesthetic composition comprises about 60% by weight the anesthetic agent, and about 40% by weight the excipient. Examples of anesthetic agents having applications herein include, but are not limited to, bupivacaine, ropivacaine, dibucaine, procaine, chloroprocaine, prilocaine, mepivacaine, etidocaine, tetracaine, lidocaine, benzocaine, or a mixture thereof. Likewise, numerous excipients have applications herein, e.g., a saturated polyglycolyzed glyceride, a block copolymer surfactant, an emulsifier, glyceryl monolaurate, silicone (condensation cured silicone elastomer), or a mixture thereof, to name only a few. In a particular embodiment, the anesthetic composition comprises about 60% by weight lidocaine and about 40% by weight a saturated polyglycolyzed glyceride, e.g., lauroyl macrogolglyceride, stearoyl macrogolglyceride, etc. In another embodiment, the excipient comprises a block copolymer surfactant.

Furthermore, the present invention extends to a method for locally delivering and immediately releasing lidocaine to the cervical region of a female in order to temporarily anesthetize the cervical region, comprising the steps of:

(a) providing a ring having an inner surface, an outer surface, a lower surface, an upper surface, and a channel on the outer surface, wherein the ring is comprised of ethylene-vinyl acetate copolymer, has a sufficient size such that it can be inserted into the vaginal canal of the female and retained therein temporarily;

(b) providing an anesthetic composition located within the channel, wherein the anesthetic composition comprises about 60% by weight lidocaine and about 40% by weight an excipient;

(c) inserting the ring into the vaginal canal of the female so that the anesthetic agent is immediately released from the anesthetic composition, and induces temporary anesthesia in the female's cervical region; and (d) removing the ring from the vaginal canal after inducing temporary anesthesia of the cervical region either prior to or after the performance of a gynecological procedure.

Examples of excipients having applications in such a method of the invention include a saturated polyglycolyzed glyceride, such as lauroyl macrogolglyceride or stearoyl macrogolglyceride, or a block copolymer surfactant.

Accordingly, it is an object of the invention to provide a new and useful apparatus for locally anesthetizing the cervical region of a female, which immediately releases an anesthetic agent directly to the vaginal mucosa of the cervical region. As a result, the cervical region is temporarily anesthetized prior to the performance of a gynecological procedure on the female.

It is another object of the invention to provide an apparatus for locally delivering and immediately releasing an anesthetic agent in the cervical region of a female that is easy to use and readily lends itself to use in an out-patient setting. These and other aspects of the present invention will be better appreciated by reference to the following drawings and Detailed Description.

The anesthetic compositions comprise 60% lidocaine by weight and 40% "GELUCIRE 44/14" lauroyl macrogolglyceride (Gattefossé S.A., Saint-Priest Cedex, France) (♦), and 60% lidocaine by weight and 40% "GELUCIRE 50/13" stearoyl macrogolglyceride (Gattefossé S.A., Saint-Priest Cedex, France) (O), respectively.

FIG. 2(B) is a graph of the comparison of the release of lidocaine from anesthetic compositions in an embodiment of the invention using a ring as schematically shown in FIG. 1. The anesthetic compositions comprise 60% lidocaine by weight and 40% "GELUCIRE 44/14" lauroyl macrogolglyceride (Gattefossé S.A., Saint-Priest Cedex, France) (♦);60% lidocaine by weight and 40% "PLURONIC F38" polyoxypropylene-polyoxyethylene block copolymer surfactant (BASF Corporation, Mt. Olive, N.J.) (O); and 60% lidocaine by weight, 20% "ABIL B8843" polyethersiloxane emulsifier (Goldschmidt Chemical Corp., Hopewell, Va.) and 20% by weight "NATROSOL" hydroxyethylcellulose (♦).

Figures 3A, 3B, 3C:
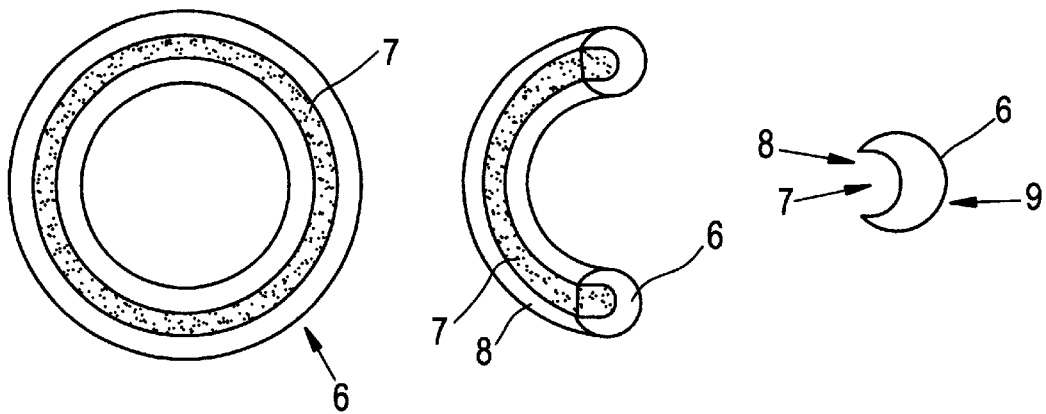

FIG. 3(A) is a schematical view of either the upper or lower surface of a ring of an embodiment of an apparatus of the invention, wherein the at least one depression comprises a channel on either the upper or lower surface of the ring. The ring has a width of 8.5 mm, and a diameter of 5.5 cm. The channel has a width of 3 mm and a depth of 4 mm.

FIG. 3(B) is a schematical view of the side of a ring of an apparatus of the invention, wherein the at least one depression comprises a channel on either the upper surface or lower surface of the ring.

FIG. 3(C) is a schematical cross sectional view of a ring of an apparatus of the invention, wherein the at least one depression comprises a channel on either the upper surface or lower surface of the ring.

Figure 4:
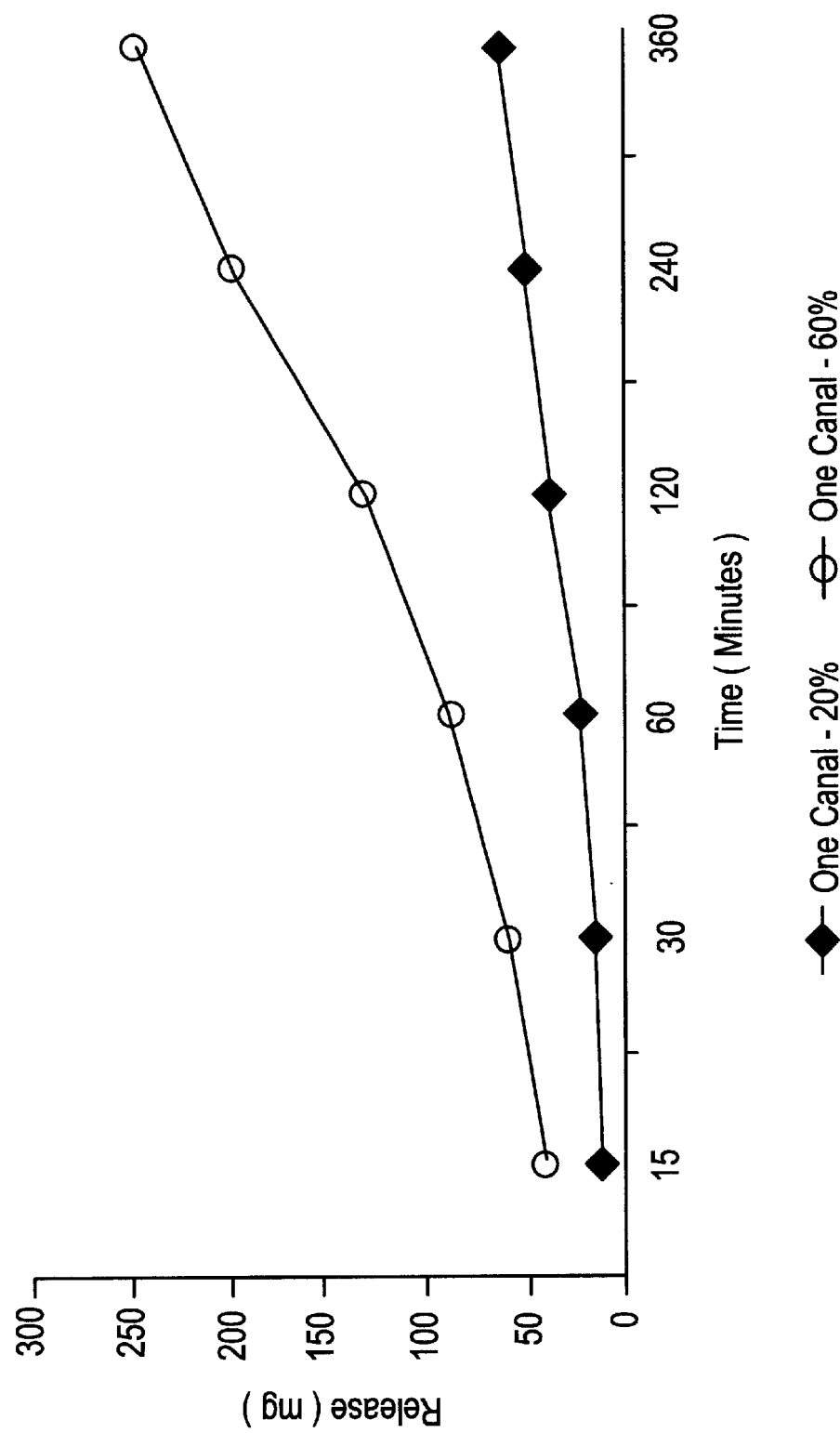

FIG. 4 is a graph of the comparison of the release of lidocaine from a pharmaceutical composition comprising 20% lidocaine by weight and 80% by weight condensation cured silicone elastomer (♦); and 60% lidocaine by weight and 40% condensation cured silicone elastomer by weight (O) respectively, in an apparatus of the invention wherein the ring is as schematically shown in FIG. 3.

FIG. 5(A) is a schematical view of a ring of either the upper surface or lower surface of a ring of an embodiment of an apparatus of the invention, wherein the at least one depression comprises a first channel on the upper surface of the ring, and a second channel on the lower surface of the ring. The ring has a width of 8.5 mm, and a diameter of 5.5 cm. The first and second channels have a width of 3 mm and a depth of 3 mm.

FIG. 5(B) is a schematical view of the side of a ring of an embodiment of an apparatus of the invention, wherein the at least one depression comprises a first channel on the upper surface of the ring, and a second channel on the lower surface of the ring.

FIG. 5(C) is a schematical cross sectional view of a ring of an embodiment of an apparatus of the invention, wherein the at least one depression comprises a first channel on the upper surface of the ring, and a second channel on the lower surface of the ring.

Figure 6:
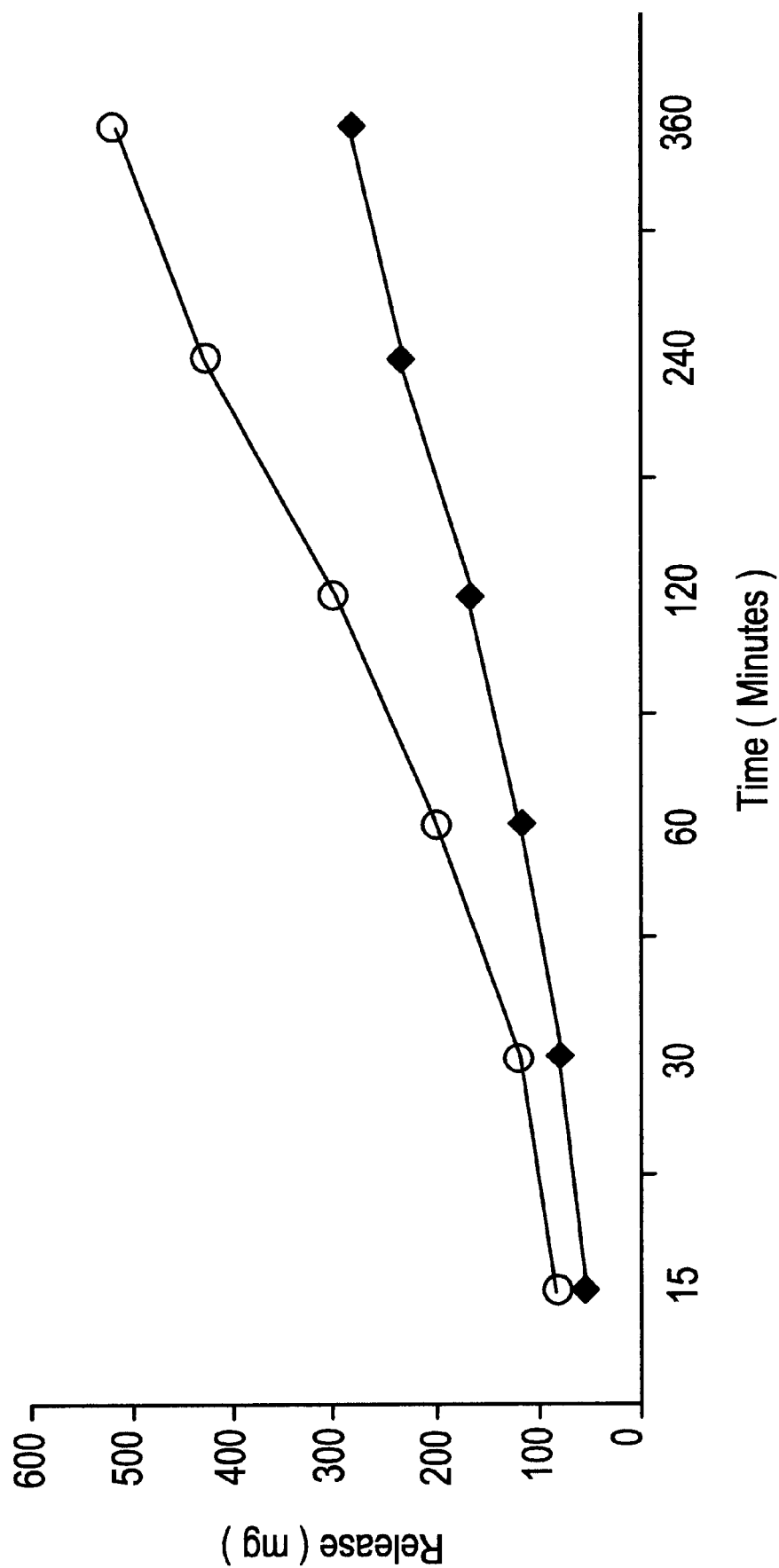

FIG. 6 is a graph of the comparison of the release of lidocaine from a pharmaceutical composition comprising 30% lidocaine by weight and 70% by weight condensation cured silicone elastomer (♦); and 60% lidocaine by weight and 40% condensation cured silicone elastomer by weight (O) respectively, in an embodiment of an apparatus of the invention wherein the at least one depression comprises a first channel on the upper surface of the ring, and a second channel on the lower surface of the ring.

Figure 7A:
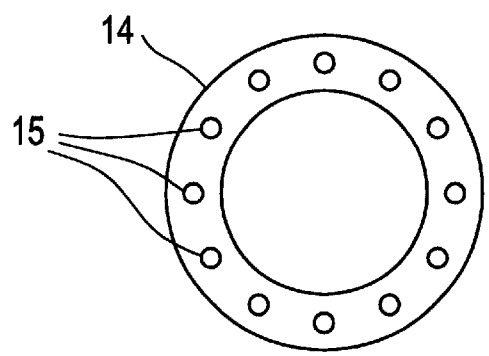

FIG. 7(A) is a schematical cross sectional view of a ring of an apparatus of the invention, wherein the at least one channel comprises 12 bores, wherein each bore runs through the ring from the upper surface of the ring to the lower surface of the ring. The ring has a width of 8.5 mm, and a diameter of 5.5 cm. Each of the bores has a width of 2 mm.

Figure 7B:
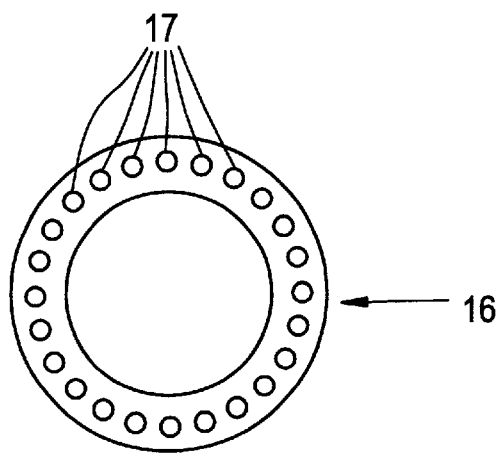

FIG. 7(B) is a is a schematical cross sectional view of a ring of an apparatus of the invention, wherein the at least one channel comprises 24 bores, each bore having a width of 2 mm, and running through the ring from the upper surface of the ring to the lower surface of the ring. The ring has a width of 8.5 mm, and a diameter of 5.5 cm. Each of the bores has a width of 2 mm.

Figure 8:
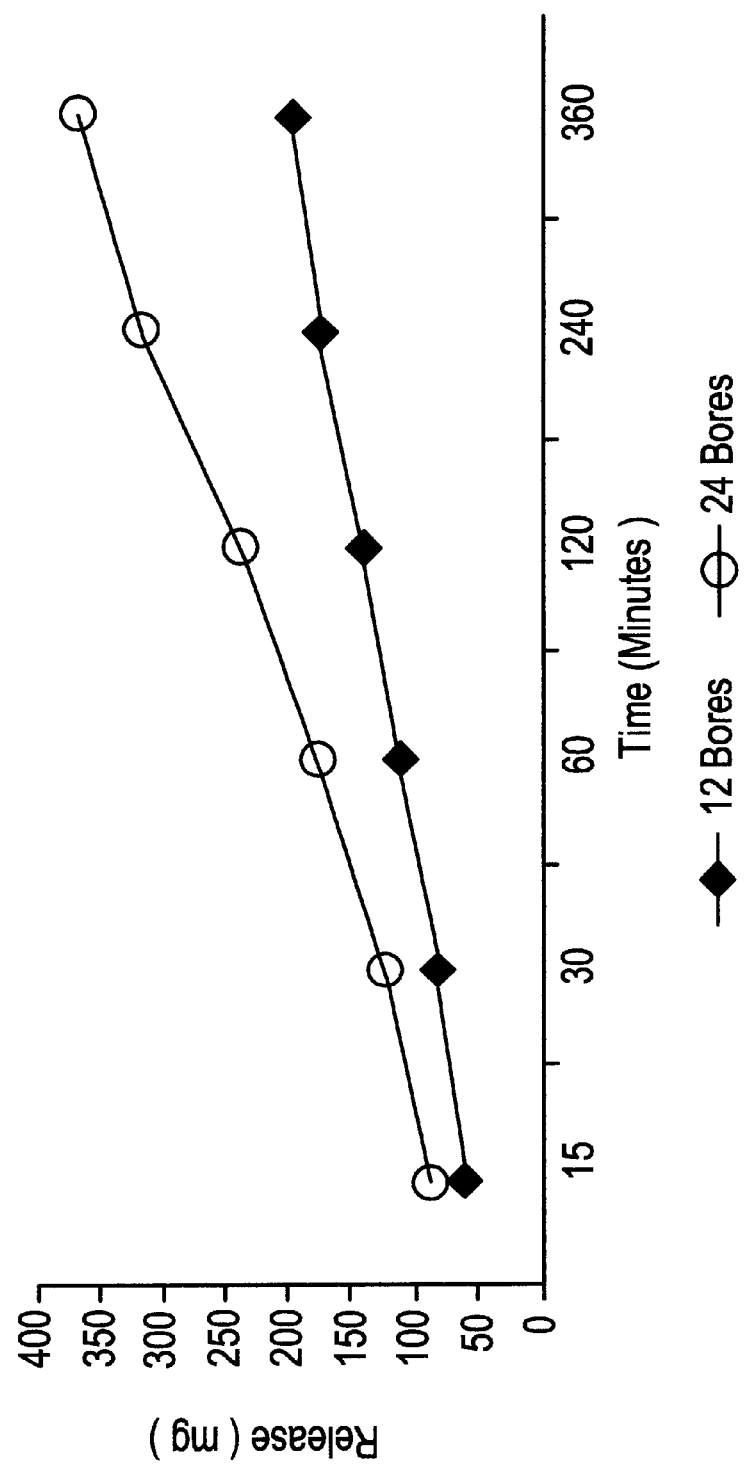

FIG. 8 is a graph of the comparison of the release of lidocaine from pharmaceutical composition comprising 60% lidocaine by weight and 40% by weight condensation cured silicone elastomer from a ring of an apparatus of the invention wherein the at least one depression comprises 12 bores, each bore having a width of 2 mm, and running through the ring from the upper surface of the ring to the lower surface of the ring (♦); and from a ring of an apparatus of the invention wherein the at least one depression comprises 24 bores, each bore having a width of 2 mm, and running through the ring from the upper surface of the ring to the lower surface of the ring (O) respectively.

FIG. 9(A) is a schematical view of a ring of an apparatus of the invention, wherein the at least one depression comprises 8 notches on the outer surface of the ring. The ring has a width of 8.5 mm, and a diameter of 5.5 cm. Each notch has a width of about 2–3 cm and a depth of about 6–8 mm.

FIG. 9(B) is a schematical view of the side of a ring of an apparatus of the invention, wherein the at least one depression comprises 8 notches on the outer surface of the ring.

Figure 10:
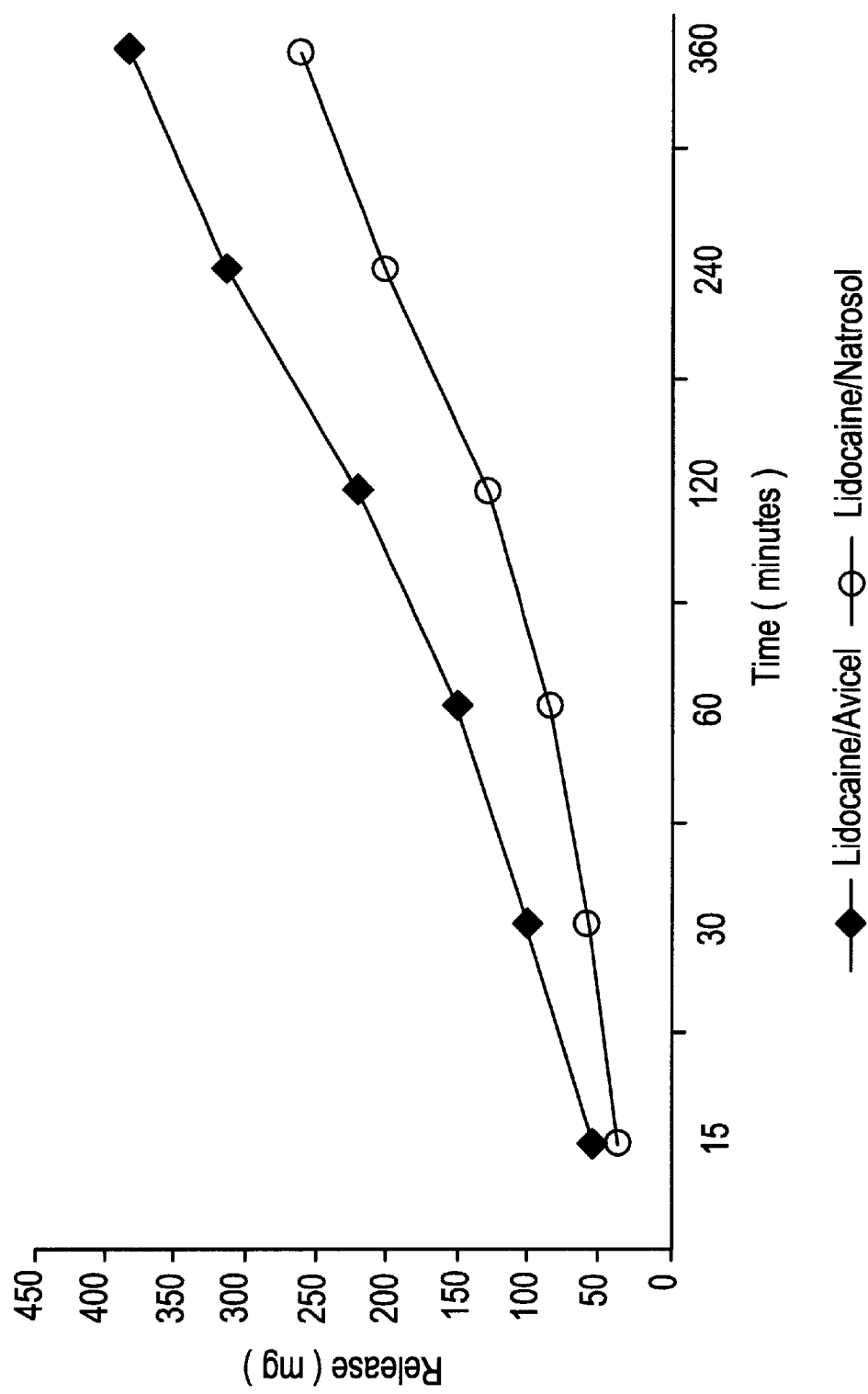

FIG. 10 is a graph of the comparison of the release of lidocaine from pharmaceutical composition from a ring as schematically shown in FIG. 9, wherein the pharmaceutical composition comprises 60% lidocaine by weight and 40% by weight microcrystalline cellulose (♦); and 60% lidocaine by weight and 40% by weight hydroxyethylcellulose (O), respectively.

Figure 11:
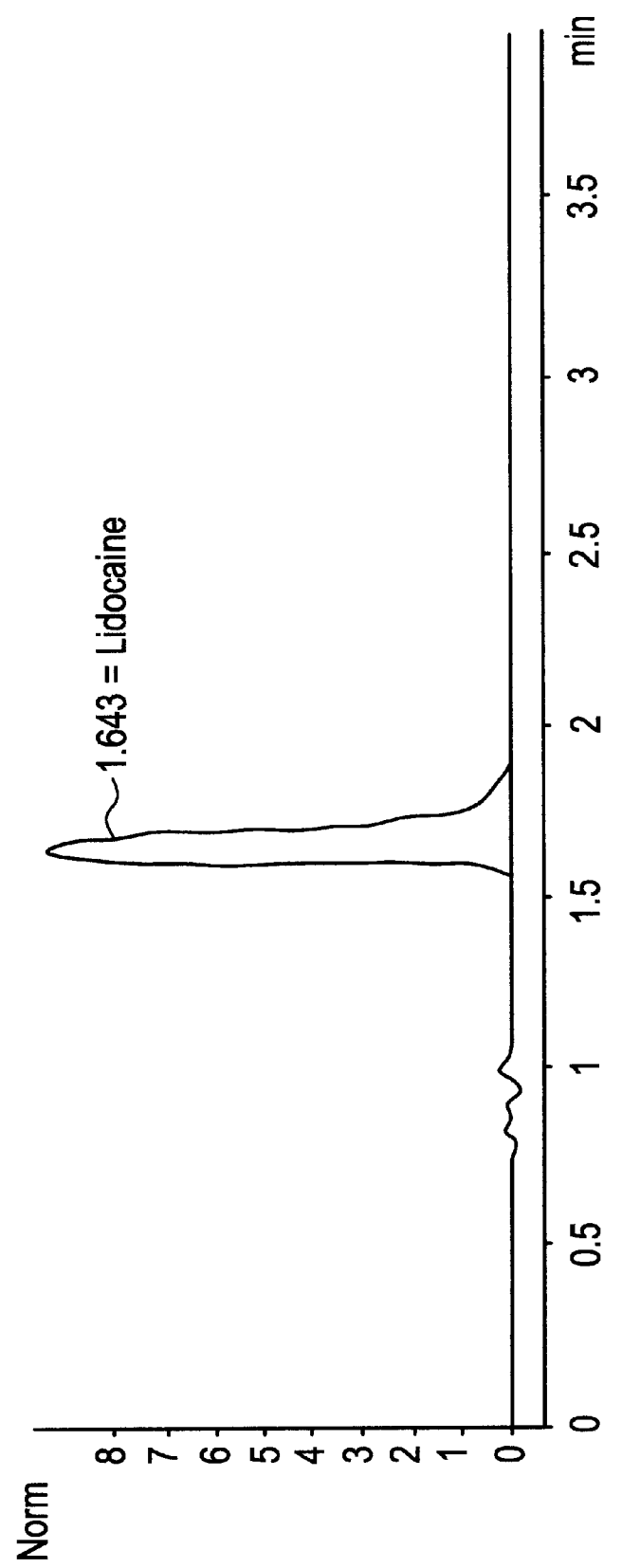

FIG. 11 is the chromatogram for lidocaine standards.

Figure 12:
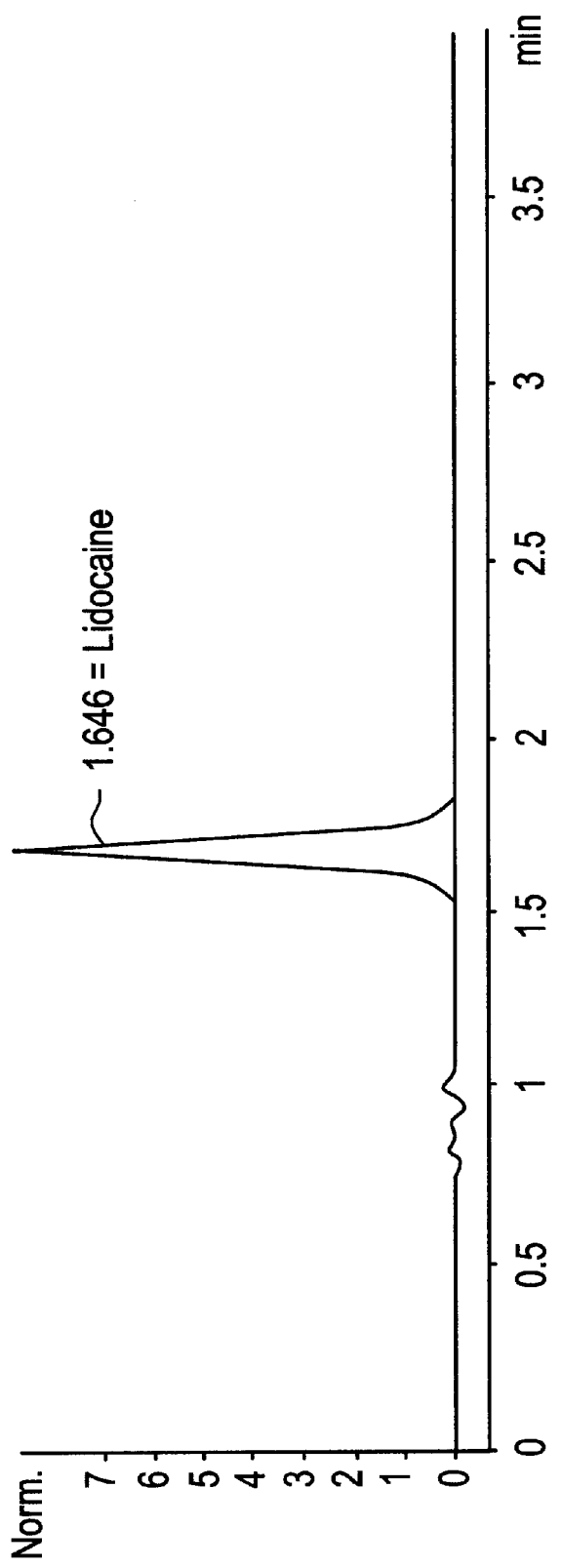

FIG. 12 is a chromatogram for a drug release profile sample.

DETAILED DESCRIPTION OF THE INVENTION

The present invention is based upon the discovery that, surprisingly and unexpectedly, a ring having at least one depression on its surface, wherein the at least one depression is filled with an anesthetic composition comprising an anesthetic agent and an excipient can locally deliver and immediately release the anesthetic agent directly to the vaginal mucosa of the cervical region when the ring is inserted into the vaginal canal of a female. In particular, an apparatus of the invention can locally deliver and immediately release up to 400 mg of an anesthetic agent, such as lidocaine, to the vaginal mucosa so that the cervical region is temporarily anesthetized in anticipation of the performance of a gynecological procedure on the female.

Thus, the present invention extends to an apparatus for delivering an anesthetic agent to the cervical region of a female; the apparatus comprising:
(a) a ring having a surface, and at least one depression on the surface, wherein the ring is comprised of a pharmaceutically acceptable inert material, and has a sufficient size such that it can be inserted into the vaginal canal of the female and retained therein temporarily;

(b) an anesthetic composition within the at least one depression, wherein the anesthetic composition comprises the anesthetic agent and an excipient.

The present invention also extends to a method for anesthetizing the cervical region of a female comprising the steps of:

(a) providing a ring having a surface, at least one depression on the surface, and an anesthetic composition located within the at least one depression and comprising an anesthetic agent and an excipient, wherein the ring is comprised of a pharmaceutically acceptable inert material, and has a sufficient size such that it can be inserted into the vaginal canal of the female and retained therein temporarily; and (b) inserting the ring into the vaginal canal of the female so that the anesthetic agent is immediately released from the anesthetic composition, contacts the female's vaginal mucosa, and locally anesthetizes the female's cervical region.

Furthermore, numerous terms and phrases are used regularly throughout the instant Specification and appending claims. Accordingly, as used herein, an "anesthetic agent" refers to a pharmacologically active agent that blocks nerve conduction when applied in a therapeutically effective amount. It can be used for either local or systemic effects. Application of an anesthetic agent means the direct contact of the anesthetic agent to the tissue to be anesthetized, such as skin or mucous membrane. An anesthetic agent having applications herein can be in the form of a free base or an acid addition salt. Particular examples or anesthetic agents having applications herein include bupivacaine, ropivacaine, dibucaine, procaine, chloroprocaine, prilocaine, mepivacaine, etidocaine, tetracaine, lidocaine, or mixtures thereof.

As used herein, the term "excipient" refers to a pharmaceutically acceptable diluent, adjuvant, carrier, or vehicle with which an anesthetic agent is administered. Such excipients can be sterile liquids, such as water and oils, including those of petroleum, animal, vegetable or synthetic origin, such as peanut oil, soybean oil, mineral oil, sesame oil and the like. Examples of excipients having applications herein include a saturated polyglycolyzed glyceride, a block copolymer surfactant, emulsifier, glyceryl monolaurate, silicone, e.g., condensation cured silicone elastomer, microcrystalline cellulose, hydroxyethylcellulose, ethylcellulose, hydroxypropyl methylcellulose, polymethylmethacrylate, polyvinylpyrollidone, or a mixture thereof.

As used herein, the term "glyceride" refers to vegetable or animal derived fatty acid esters of glycerol.

As used herein, the phrase "saturated polyglycolyzed glyceride" refers to mixtures of glycerides and polyethylene glycolesters. As explained above, any saturated polyglycolyzed glyceride presently known or subsequently discovered has applications in an apparatus of the invention.

As used herein, the term "surfactant" refers to chemical compounds which have both hydrophilic and hydrophobic properties. Adding a surfactant to a solvent promotes the solubilization of a substance into the solvent.

As used herein, the phrase "block copolymer" refers to monomer units or repeating units of surfactant which occur at regular intervals in a substance and are always found in a particular configuration.

As used herein, the term "emulsifier" refers to a substance, which enables the suspension of small globules of one liquid into a second immiscible liquid.

As used herein, the term "temporary" (including various forms, such as temporarily) means lasting, used or serving for a limited period of time.

As used herein, the phrase "lauroyl maci-ogolglyceride" refers to a saturated polyglycolyzed glyceride comprising mono, di and triesters of glycerol and monoesters and diesters of macrogols (mainly of lauric acid) with a mean relative molecular weight between 300–1500 D.

As used herein, the term "depression" on a surface of a ring refers to an area of the surface that is sunk below its surroundings. Particular examples of depressions having applications herein include, but certainly are not limited to notches, channels and bores on a surface of a ring.

As used herein, the phrase "vaginal canal" refers to a canal which runs from the hymenal ring to the cervix of a female (also referred to as the vagina) and the fornices surrounding the vagina.

As used herein, the phrase "pharmaceutically acceptable inert material" referring to the material of which a ring of an apparatus of the invention is constructed, refers to a biocompatible material which does not dissolve or disintegrate when inserted into the body and does not exhibit pharmacological activity of its own. Examples of such materials include, but are not limited to ethylene-vinyl acetate copolymer, polyethylene, polypropylene, polyurethane, polyvinylchloride, cellulose derivatives, thermoplastic rubber, thermoplastic elastomer, or polydimethylsiloxane, to name only a few.

As used herein, the term "biocompatible" refers to a material having the property of being biologically compatible by not producing a toxic, injurious, or immunological response in living tissue.

As used herein, the phrase "pharmaceutically acceptable" refers to molecular entities, excipients, and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the US Pharmacopoeia or other generally recognized pharmacopoeia for use in animals, and more particularly in humans.

The phrase "therapeutically effective amount" is used herein to mean an amount sufficient to reduce pain by at least about 15 percent, preferably by at least 50 percent, more preferably by at least 90 percent, and most preferably prevent, a clinically significant pain for the patient. Alternatively, a therapeutically effective amount is sufficient to cause an improvement in a clinically significant condition in the host.

As used herein, the phrase "immediate release" refers to the uncontrolled release of an anesthetic agent from an anesthetic composition, wherein the anesthetic composition does not comprise a composition which would retard the release of the anesthetic agent from the anesthetic composition, and prolong and sustain the release of the anesthetic agent.

As used herein, the term "anesthesia" refers to the condition of, e.g., a local numbness and/or analgesia and/or inhibitory effects on sensory and motor function, induced, by way of contact with an anesthetic agent described above.

As explained above, FIG. 1(A) is a schematical view of the upper surface of a ring of the apparatus of the invention. Ring (1) comprises an upper surface (3), a lower surface (not shown), an inner surface (4) and an outer surface (5). Channel (2) is located on outer surface (5). Ring (1) is made of a pharmaceutically acceptable inert material such as silicone, ethylene-vinyl acetate copolymer, polyethylene, polypropylene, polyurethane, polyvinylchloride, cellulose derivatives, thermoplastic rubber, thermoplastic elastomer, polydimethylsiloxane, etc. In a particular embodiment, the inert pharmaceutically acceptable material is ethylene-vinyl acetate copolymer. Furthermore, the size of ring (1) can vary depending upon its application. In a particular embodiment of the invention, wherein the female is a human female, ring (1) has cross sectional width of 8.5 mm and a diameter of 5.5 cm, wherein the diameter is measured from the center of the hole formed within the ring to the outer surface of the ring. In an embodiment of the invention, channel (2) is filled with an anesthetic composition comprising an anesthetic agent and an excipient. Numerous anesthetic agents in a free base form, an acid addition salt form, or a mixture thereof, have applications in an anesthetic composition of the invention. Particular examples of such anesthetic agents include, but certainly are not limited to bupivacaine, ropivacaine, dibucaine, procaine, chloroprocaine, prilocaine, mepivacaine, etidocaine, tetracaine, lidocaine, benzocaine, or a mixture thereof. In a particular embodiment, the anesthetic agent is lidocaine. Furthermore, numerous excipients have applications herein, and are described above.

Figure 1A:
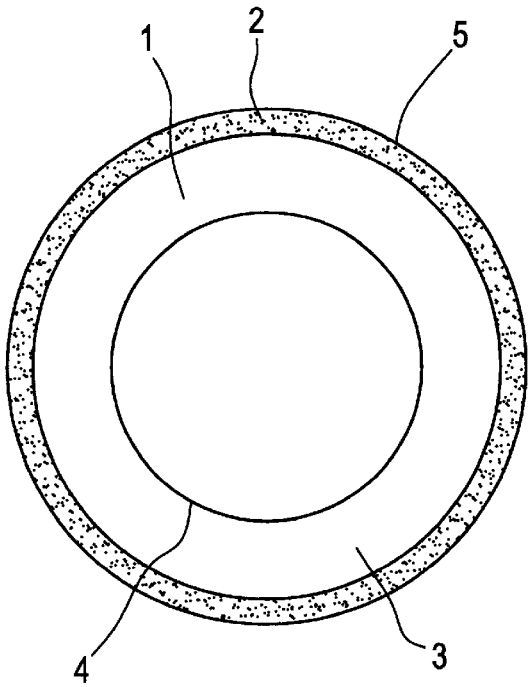
FIG. 1(A) is a schematical view of the upper surface of a ring of an embodiment of an apparatus of the invention, wherein the at least one depression comprises a channel on the outer surface of the ring. The ring has a width of 8.5 mm, and a diameter of 5.5 cm. The channel has a width of 3 mm and a depth of 4 mm.
Figure 1B:
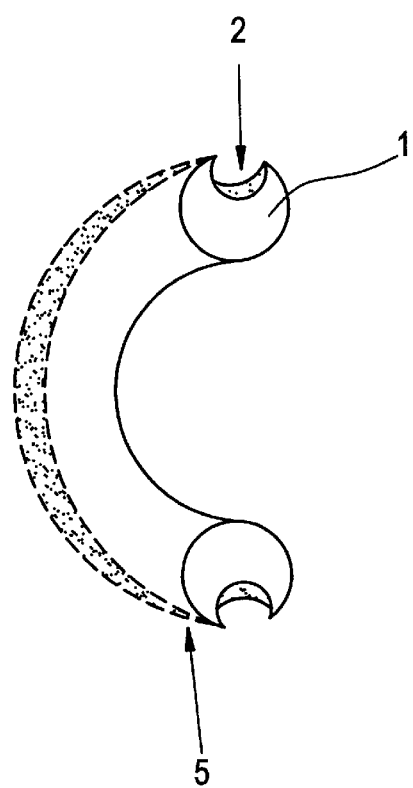
FIG. 1(B) is a schematical view of the side of a ring of an embodiment of an apparatus of the invention, wherein the at least one depression comprises a channel on the outer surface of the ring.
Figure 1C:
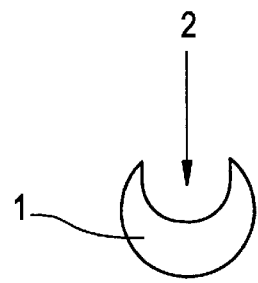
FIG. 1(C) is a schematical cross sectional view of a ring of the apparatus of the invention, wherein the at least one depression comprises a channel on the outer surface of the ring.

FIG. 1(B) is a schematical view of the side of a ring of the apparatus of the invention. Again, channel (2) can be seen on outer surface (5) of ring (1). FIG. 1(C), a schematical cross sectional view of ring (1), clearly shows channel (2). The depth of channel (2) is 4 mm and the width of channel (2) is 3 mm.

FIG. 3(A) is a schematical view of an apparatus of the invention, wherein the at least one depression comprises a channel on either the upper or lower surface of the ring. In particular, ring (6) is comprised of a pharmaceutically acceptable inert material, such as silicone, ethylene-vinyl acetate copolymer, polyethylene, polypropylene, or polyurethane, to name only a few. Moreover, ring (6) has cross-sectional width of 8.5 cm and a diameter of 5.5 cm, such that it can be inserted into the vaginal canal of a human female. However, the size of the ring can vary, depending upon whether the female is bovine, feline, canine, porcine, etc. The at least one depression on the surface of ring (6) comprises channel (7). Naturally, channel (7) can be located on either the upper or lower surface of ring (6).

FIG. 3(B) is a schematical side view of a ring of an apparatus of the invention, wherein the at least one depression comprises a channel on either the upper or lower surfaces of the ring. More specifically, FIG. 3(B) schematically shows ring (6) having channel (7) on surface (8), wherein surface (8) is either the upper surface or lower surface of ring (6). FIG. 3(C) is a schematical cross sectional view of the ring (6), having channel (7) on either the upper or lower surfaces (8). Channel (7) has a width of 3 mm and a depth of 4 mm.

FIGS. 5(A)–(C) schematically show another embodiment of an apparatus of the invention, wherein the at least one depression on the ring comprises a first channel on the upper surface of the ring, and a second channel on the lower surface of the ring. More specifically, FIG. 5(A) schematically shows upper surface (10) of ring (9). Ring (9) is comprised of a pharmaceutically acceptable inert material, and having a sufficient size such that it can be inserted into the vaginal canal of a female. In a particular embodiment of the invention, ring (9) has a width of 8.5 mm and a diameter of 5.5 cm. The at least one depression in this embodiment of an apparatus of the invention comprises first channel (11) on upper surface (10), and a second channel (not shown) on a lower surface (not shown) of ring (9). FIGS. 5(B)–(C) schematically show lower surface (12) and second channel (13), and their relation to first channel (11) on upper surface (10). First channel (11) and second channel (13) each have a width of 3 mm and a depth of 3 mm.

FIGS. 7(A) and (B) show cross sectional schematical views of rings having applications in an apparatus or method of the invention, wherein the rings have a plurality of bores through the rings. In particular, FIG. 7(A) schematically shows ring (14) that has twelve (12) bores (15) which run from the upper surface (not shown) of ring (14) to the lower surface (not shown) of ring (14). FIG. 7(B) schematically shows a ring (16) having twenty-four (24) bores running from the upper surface to the lower surface. As explained above, numerous pharmaceutically acceptable materials having applications in ring (14). Particular examples include, but certainly are not limited to silicone, ethylene-vinyl acetate copolymer, polyethylene, polypropylene, polyurethane, polyvinylchloride, cellulose derivatives, thermoplastic rubber, thermoplastic elastomer, polydimethylsiloxane, etc, and in a particular embodiment, the inert pharmaceutically acceptable material is ethylene-vinyl acetate copolymer. As explained above, rings (14) and (16) should have sufficient size such that it can be inserted into the vaginal canal of a female, and remain therein temporarily. In a particular embodiment, wherein the female is a human female, rings (14) and (16) have a width of 8.5 mm and a diameter of 5.5 cm. Since bores (15) and (17) run from the upper surface to the lower surface of rings (14) and (16) respectively, bores (15) and (17) have a length of 8.5 mm. The width of bores (15) and (17) is 2 mm. A pharmaceutical composition comprising a pharmaceutical agent and an excipient is then placed within bores (15) and (17), and the ring is then inserted into the vaginal canal of a female, wherein the anesthetic agent is immediately released to induce anesthesia in the cervical region.

FIG. 9(A) and (B) are schematical views of a ring having applications herein, wherein the ring has a plurality of notches on its outer surface. In particular, FIG. 9(A) schematically shows the cross section of ring (18), which has outer surface (19), inner surface (20), along with an upper and a lower surface (not shown). The dimensions of ring (18) and notches (20) can vary depending upon the type of female being anesthetized and the quantity of anesthetic agent that is to be locally delivered and immediately released. In a particular embodiment, wherein the female is a human female, ring (18) has a width of 8.5 mm, and a diameter of 5.5 cm, and notches (20) have a width of about 2–3 cm and a depth of about 6–8 mm. Also, notches (20) are spatially arranged on outer surface (19). A pharmaceutical composition comprising an anesthetic agent and an excipient is then placed within the notches. The ring is then inserted into the vaginal canal of the female, and the anesthetic agent is immediately released.

The present invention may be better understood by reference to the following non-limiting Example, which is provided as exemplary of the invention. The following Examples are presented in order to more fully illustrate the preferred embodiments of the invention. They should in no way be construed, however, as limiting the broad scope of the invention.

EXAMPLES

Anesthetic agents are pharmacologically active agents that block nerve conduction when applied in therapeutically effective amounts. They have been used for either local or systemic effects. Currently, anesthetics are being extensively used in the medical field for topical or local anesthesia.

Application of a topical or local anesthetic means direct contact of the anesthetic with the tissue to be anesthetized, such as the skin or mucous membrane, e.g., vaginal mucosa.

Many gynecological procedures are performed in an out-patient setting instead of at the hospital. Current techniques used in the application of local anesthetic agents for such procedures include, among others, paracervical injections as well as the use of cervical sprays, creams and ointments. These cervical anesthetic application techniques are labor intensive, time consuming, expensive, and difficult to perform. Only a trained medical professional can perform local anesthetic applications in the cervical region and, as a result, this procedure is often not performed prior to a gynecological procedure. This causes a great deal of pain and discomfort to the patient undergoing the gynecological procedure.

The use of an immediate release transvaginal ring (TVR) product containing a local anesthetic agent would provide a simple, safe, rapid and inexpensive alternative to both medical professionals and patients alike. The TVR could be inserted into the patient by a medical professional or it could be self-administered. The inserted ring would be removed either before or after the performance of the gynecological procedure. The objective of the experiments reported herein is to develop an immediate release TVR product comprising an anesthetic agent, wherein the product can be used easily by medical providers or women patients.

Generally, local anesthetic agents are benzoic acid ester or amide derivatives of aniline (either substituted or unsubstituted), and are administered as a free base or the acid addition salt. To be effective, a local anesthetic agent should be present in therapeutically effective amounts to produce an anesthetic effect. It should penetrate the vaginal mucosa sufficiently to deliver the therapeutic dose to the surrounding tissues, and it should exhibit a rapid onset of action and have a good prolonged anesthetic effect. Various configurations of a ring of the invention were examined, and the results of such examinations are set forth below.

As explained above, the anesthetic composition used in a ring of an apparatus of the invention comprises an anesthetic agent and an excipient. Numerous anesthetic agents can be used in an anesthetic composition, including, but not limited to bupivacaine, ropivacaine, dibucaine, procaine, chloroprocaine, prilocaine, mepivacaine, etidocaine, tetracaine, lidocaine, or mixtures thereof. In the embodiments of the invention set forth infra, the anesthetic agent used in the anesthetic composition is lidocaine from Sigma Chemical Company, St. Louis, Mo., having a Chemical Abstracts Number (CAS) 137–58–6 and Sigma Company Catalog number L7757.

Furthermore, various excipients are used in the anesthetic compositions having applications in embodiments of the invention set forth infra. In particular, in order to form the anesthetic compositions, the anesthetic agent must be blended with the excipient. Numerous excipients, including saturated polyglycolyzed glycerides, block copolymer surfactants, emulsifiers, glyceryl monolaurate, silicone (cured silicone elastomer), microcrystalline cellulose, hydroxyethylcellulose, ethylcellulose, hydroxpropyl methylcellulose, polymethyl methacralate, polyvinylpyrollidone, or a mixture thereof, to name only a few, have applications in an apparatus and method of the invention. Particular examples of saturated polyglycolyzed glycerides, block copolymer surfactants, and emulsifiers are set forth below. However, an apparatus or method of the present invention should in no way be construed as limited to the use of these particular excipients. Table 1 shows examples of excipients having applications herein and their Hydrophilic-Lipophilic Balance (HLB) values.

TABLE 1

High HLB System Excipients

| Excipient | Description | Form | HLB Value |
| --- | --- | --- | --- |
| Gelucire 44/14 | Polyglycolyzed Glycerides | Hard Wax | 14 |
| Gelucire 50/13 | Polyglycolyzed Glycerides | Hard Wax | 13 |
| Pluronic F38 | Black Copolymer Surfactant | Low Melting Pellets | 31 |
| Pluronic F68LF | Block Copolymer Surfactant | Low Melting Pellets | 26 |
| Abil B8843 | Emulsifier | Viscous Liquid | 26 ± 2 |
| Myverol 18-92K | Glyceryl Monolaurate | Very Soft Wax | unknown |

Other Excipients having Applications herein are described in Table 2:

TABLE 2

| Trade Name | Description |
| --- | --- |
| "AVICEL" | Microcrystalline Cellulose |
| "NATROSOL" | Hydroxyethylcellulose |
| "ETHOCEL" | Ethylcellulose |
| "METHOCEL" | Hydroxypropyl Methylcellulose |
| "EUDRAGIT" | Polymethylmethacrylate |
| "KOLLIDON" | Polyvinylpyrollidone |

All of these excipients are can be readily obtained by one of ordinary skill in art.

METHODS

Drug Release Profile (DRP) Experiments

DRP experimentation was performed on anesthetic compositions comprising lidocaine. Samples were placed in a USP dissolution apparatus II (Distek) with 900 mL of simulated vaginal fluid (SVF). The bath was heated to 37° C. Samples were placed in ring holders and placed on the bottom of the vessel. Paddles were used to circulate the SVF at a speed of 50 rpm.

The simulated fluid was composed of 0.1 M potassium acetate, 0.1 M glacial acetic acid and sodium chloride salt. These were mixed in a proportion of 28.5%:71.5%, with the salt being added in the amount of 4.7 grams per liter of solution. This yielded a solution with a pH of 4.2, which is similar to that of vaginal fluid.

1 mL samples were removed at 15, 30, 60, 120, 240 and 360 minute intervals. The samples were placed into HPLC vials, capped and held for analysis.

High Performance Liquid Chromatography Conditions

A method based on chromatographic separation was used to determine the drug concentration from drug release profile (DRP) samples.

The high performance liquid chromatography (HPLC) method was found to be linear over a range from 5 $\mu$g/mL to 500 $\mu$g/mL. The retention time ($t_r$) was found to be approximately 1.7 minutes (see FIG. 11).

The following chromatographic conditions were used:
System: Hewlett Packard 1100 liquid chromatograph with UV detection
Column: Alltech Rocket Platinum EPS C18, 3 $\mu$, 53×7 mm ID
Mobile Phase: 60% 0.05 M Potassium Phosphate: 40% Acetonitrile pH 3.0

Detector wavelength: 262 nm
Flow Rate: 1.5 mL/min
Injection volume: 5 µL
Column Temperature: 40° C.
Run Time: 4 minutes
Quantitation: Peak Area A. Ethylene-Vinyl Acetate Copolymer (EVA) Rings Having a Channel on Either the Upper or Lower Surface of the Ring Utilizing EVA rings having a diameter of 5.5 cm and cross sectional width of 8.5 mm, a channel was drilled into the upper surface of each EVA ring, wherein the channel had a width of 3 mm and a depth of 4 mm. See FIGS. 3(A)–(C). The channel was filled with an anesthetic composition comprising lidocaine and an excipient comprising saturated polyglycolyzed glyceride and condensation cured silicone elastomer, wherein the excipient ranged in concentration from 20% by weight of the anesthetic composition to 60% by weight of the anesthetic composition. The rings were then tested for the immediate release of lidocaine using the drug release protocol set forth above.

The results of the study, graphically shown in FIG. 4, show that an apparatus of the invention wherein the ring comprises a channel on either upper or lower surface of the ring immediately releases the anesthetic agent under conditions found in the vaginal canal of a female.

B. Ethylene-Vinyl Acetate Copolymer Rings Having a First Channel on the Upper Surface of the Ring, and a Second Channel on the Lower Surface of the Ring First and second channels were drilled into the upper and lower surfaces respectively of an ethylene-vinyl acetate copolymer ring having a diameter of 5.5 cm, a cross-sectional width of 8.5 mm. Such a ring is schematically shown in FIGS. 5(A)–(C). The first and second channels had a width of 3 mm, and a depth of 3 mm. The first and second channels were then filled with a pharmaceutical composition comprising lidocaine and an excipient, wherein the excipient comprised "GELUCIRE $^{44}/_{14}$" lauroyl macrogolglyceride (Gattefossé S.A. Saint-Priest Cedex, France) and condensation cured silicone elastomer. It should be noted however that any excipient described above has applications herein. In the anesthetic composition, the excipient ranged in concentration from 20% by weight of the anesthetic composition to 60% by weight. Thus, the lidocaine of the anesthetic composition ranged from about 80% by weight to 40% by weight. The rings were then tested for the immediate release of lidocaine using the drug release protocol set forth above. The results of this test are set forth in FIG. 7. These results show that a ring having a first channel on the upper surface, and a second channel on the lower surface, wherein each channel is filled with a pharmaceutical composition immediately released the anesthetic agent in conditions that are present in the vaginal canal of a female. An anesthetic composition comprising about 60% by weight lidocaine released a greater amount of lidocaine per unit time than did the ring having a pharmaceutical composition comprising 20% by weight lidocaine.

C. Ethylene-Vinyl Acetate Copolymer Rings Wherein the at least One Depression Comprises a Plurality of Bores Through the Ring and Running from the Upper Surface to Lower Surface of the Ring Another EVA ring design for use in an apparatus or method for locally delivering and immediately releasing an anesthetic agent to the cervical region of a female is a ring having a plurality of pores in the ring which run from the upper surface to the lower surface of the ring. Examples of such rings are set forth in FIGS. 7(A)–(B). In this embodiment, the bores were filled with a pharmaceutical composition comprising 60% by weight lidocaine and 40% by weight silicone (condensation cured silicone elastomer) excipient. The rings were then tested for the immediate release of lidocaine using the drug release profile set forth above.

The results of the drug profile experiments, graphically set forth in FIG. 8, show that both the 24-pore and the 12-pore rings immediately released lidocaine under conditions that would be encountered in the vaginal canal of the female. Thus, both configurations have applications in locally delivering and immediately releasing an anesthetic agent to the cervical region, to induce temporary anesthesia of the cervical region.

D. Ethylene-Vinyl Acetate Copolymer Rings Having a Channel on Their Outer Surface, for Delivering an Anesthetic Agent Experiments were then conducted with a ring formed of ethylene-vinyl acetate copolymer, and having a channel on its outer surface. An example of this embodiment is schematically shown in FIGS. 1(A)–(C). Experiments with this ring configuration were performed using pharmaceutical compositions with different excipients.

i. Ethylene-Vinyl Acetate Copolymer Rings with an Anesthetic Composition Comprising Lidocaine and an Excipient Comprising Saturated Polyglycolyzed Glycerides and Condensation Cured Silicone Elastomer In this experiment, the channel on the outer surface of rings as schematically shown in FIGS. 1(A)–(C) was filled with an anesthetic composition comprising 60% by weight lidocaine and 40% by weight excipient, wherein the excipient comprised 37.5% by weight saturated polyglycolyzed glyceride and 62.5% by weight condensation cured silicone elastomer. In one set of rings, the saturated polyglycolyzed glyeride was "GELUCIRE $^{44}/_{14}$ lauroyl macrogolglyceride (Gattefossé S.A., Saint-Priest Cedex, France), and in another set, the saturated polyglycolyzed glyceride was "GELUCIRE $^{50}/_{13}$" stearoyl macrogolglyceride (Gattefossé S.A., Saint-Priest Cedex, France). These saturated polyglycolyzed glycerides were softened with mixing in the Hauschild Speed Mixer, and then blended with lidocaine. After filling the channel of the rings, the rings were tested for immediate release of lidocaine using the drug profile release protocol set forth above.

Figure 2A:
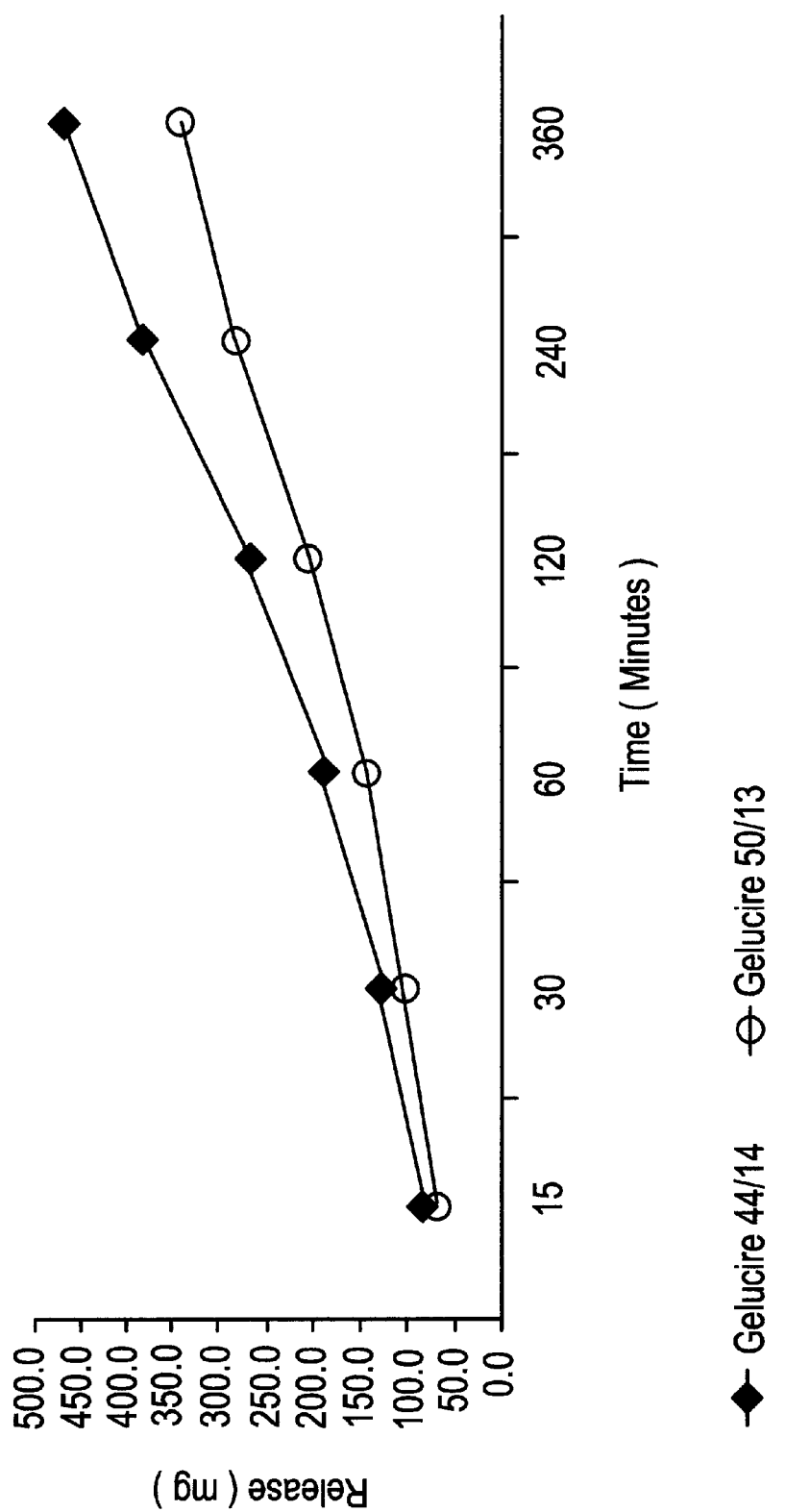
FIG. 2(A) is a graph of the comparison of the release of lidocaine from anesthetic compositions in an embodiment of the invention using a ring as schematically shown in FIG. 1.

The results of the drug release profile experiments for both sets of rings are set forth in FIG. 2(A). FIG. 2(A) graphically shows that both sets of rings immediately released lidocaine under conditions that would be encountered when such rings are inserted in the vaginal canal of a female.

ii. Ethylene-Vinyl Acetate Copolymer Rings with an Anesthetic Composition Comprising Lidocaine and a Saturated Polyglycolyzed Glyceride Excipient in a Channel on the Outer Surface of the Rings In this experiment, ethylene-vinyl acetate copolymer rings such as those used in (i) above were used. Two sets of rings were used. The channels of one set of rings had an anesthetic composition in comprising 60% by weight lidocaine and 40% by weight "GELUCIRE $^{44}/_{14}$" lauroyl macrogolglyceride excipient. The channels of the other set of rings were filled with an anesthetic composition comprising 60% by weight lidocaine and 40% by weight "GELUCIRE $^{50}/_{13}$ stearoyl macrogolglyceride excipient. The rings were then tested for the immediate release of lidocaine using the drug release profile protocol set forth above.

The results of the drug release profile experiments are graphically set forth in FIG. 2(B). In particular, FIG. 2(B) shows both rings immediately released lidocaine into the simulated vaginal fluid. In particular, the release of lidocaine after thirty minutes was greater than 400 mg. After two hours, the release reached a plateau. Upon inspection of the rings after performance of the drug release profile protocol, no anesthetic composition remained in the channel of the rings.

iii. Ethylene-Vinyl Acetate Copolymer Rings with an Anesthetic Composition Comprising Lidocaine and a Polyoxypropylene-Polyoxethylene Block Copolymer Excipient in a Channel on the Outer Surface of the Rings In this experiment, ethylene-vinyl acetate rings having a channel on their outer surface, and as described above, were used. An anesthetic composition was formed comprising 60% by weight lidocaine and 40% "PLURONIC F38" polyoxy-propylene-polyoxyethylene block copolymer surfactant (BASF Corporation, Mt. Olive, N.J.). In particular, the "PLURONIC F38" pellets were heated until just softened, and then mixed with an appropriate amount of lidocaine. The anesthetic composition was placed in the channel on the outer surface of the rings. The rings were then tested for the immediate release of lidocaine with the drug release profile protocol set forth above.

The results of drug release profile protocol are graphically set forth in FIG. 2(B). FIG. 2(B) indicates that lidocaine was immediately released from the anesthetic composition. Moreover, just as with the "GELUCIRE 44/14" lauroyl mcrogolglyceride anesthetic composition described in (ii) above, none of the anesthetic compositions comprising 60% by weight lidocaine and 40% by weight "PLURONIC F38" polyoxy-propylene-polyoxyethylene block copolymer surfactant remained in the channel of the ethylene-vinyl acetate copolymer ring after 6 hours in the simulated vaginal fluid.

iv. Ethylene-Vinyl Acetate Copolymer Rings with an Anesthetic Composition Comprising Lidocaine and an "ABIL B 8843" Polyethersiloxane Emulsifier Excipient in a Channel on the Outer Surface of the Rings Ethylene-vinyl acetate copolymer rings used in this experiment had a channel on their outer surface and an dimensions that are described above. The anesthetic composition prepared and placed into the channel on the outer surfaces of these rings comprised 60% by weight lidocaine and "ABIL B 8843" polyethersiloxane emulsifier. However, this emulsifier is a liquid and would not hold its shape in the channel of the rings. Thus, it was necessary to add hydroxyethylcellulose ("NATROSOL") to the anesthetic composition. As a result, the anesthetic composition used in this example comprised 60% by weight lidocaine, 20% by weight "NATROSOL" hydroxyethylcellulose, and 20% by weight "ABL B 8843" polyethersiloxane emulsifier. The anesthetic composition was then placed in the channel of the rings. The rings were then tested for release of the anesthetic agent using the drug release profile protocol described above.

The results of this experiment are graphically set forth in FIG. 2(B). FIG. 2(B) indicates that rings having this anesthetic composition also immediately released lidocaine under conditions that would be encountered in the vaginal canal of a female. Upon inspection of the rings after removal from the simulated vaginal fluid, it was observed that a portion of the anesthetic composition remained in the channel, and was partially swollen.

E. Ethylene-vinyl acetate copolymer Rings having a Plurality of Notches on their Outer Surface, for Delivering an Anesthetic Agent In this embodiment of the invention, the at least one depression on the surface of the ring comprises a plurality of notches on the outer surface of the ring. Particular examples are schematically shown in FIGS. 9(A) and 9(B). The ring used in this embodiment was comprised of ethylene-vinyl acetate copolymer. However, as explained above, any pharmaceutically acceptable inert material, including those having a melting point from about 60° C. to about 200° C. have applications in an apparatus of the invention. Also, the notches in this particular embodiment of the invention had a width of about 2–3 cm and a depth of about 6–8 mm.

Furthermore, as explained above, the anesthetic composition is placed in the notches of the ring. In particular, the anesthetic composition is a powder mix comprising lidocaine and excipients. The tablets were made in a sufficient size such that they could be firmly held in place in the notches. Particular excipients having applications herein are set forth above.

In an example of this embodiment, an anesthetic composition comprising 40% by weight "AVICEL PH-101" microcrystalline cellulose and 60% by weight lidocaine was made and compressed into tablets. Eight of the tablets were placed in the notches of ethylene-vinyl acetate copolymer rings. The rings were then tested using the drug release profile protocol set forth above for rapid release of lidocaine.

In another example of this embodiment of the invention, an anesthetic composition comprising 40% by weight "NATROSOL 250 HHX" hydroxyethylcellulose and 60% by weight lidocaine was made. The anesthetic composition was then compressed into tablets. Eight of the tablets were placed in the notches of the ethylene-vinyl acetate copolymer ring. Using the drug release profile protocol set forth above, the rings were then tested for the immediate release of lidocaine.

FIG. 10 graphically compares the release of lidocaine from both tablet systems. Upon inspection of the tablets after the study, it was observed that the almost all of the tablets were partially disintegrated. The "NATROSOL 250 HHX" hydroxyethylcellulose tablets were swollen, a phenomenon observed in the ABIL/NATROSOL combination (high-HLB formulations) described above. As FIG. 10 graphically shows, this embodiment of an apparatus of the invention has ready applications in the local delivery and immediate release of an anesthetic agent to the cervical region of the female, when used in a method of the invention.

DISCUSSION

The results of the experiments set forth above indicate that an apparatus of the invention has ready applications in locally delivering and immediately releasing an anesthetic agent to the cervical region of a female. Moreover, due to the simplicity of a method of the instant invention, special skills are not required of medical providers to use the instant invention. Thus, the number of females, particularly women, that can avoid the pain and discomfort associated with certain gynecological procedures can be increased compared to the number of women presently avoiding pain and discomfort associated gynecological procedures only by employing heretofore known expensive, technically difficult, and potentially dangerous methods of anesthetizing the cervical region.

Many other variations and modifications of the instant invention will be apparent to those skilled in the art without departing from the spirit and scope of the instant invention. The above-described embodiments are therefore, intended to be merely exemplary, and all such variations and modifications are intended to be included within the scope of the instant invention as defined in the appended claims.

Various publications are cited herein, the disclosures of which are incorporated by reference in their entireties.

What is claimed is:

1. An apparatus for locally delivering and immediately releasing an anesthetic to the cervical region of a female, said apparatus comprising:
   (a) a ring having an exterior surface with at least one depression on said exterior surface, said at least one depression adapted to receive a predetermined amount of an anesthetic composition, wherein said ring is comprised of a pharmaceutically acceptable inert material, and said ring has a sufficient size such that it can be inserted into the vaginal canal of said female; and,
   (b) an anesthetic composition located within said at least one depression, wherein said anesthetic composition comprises said anesthetic agent and an excipient which facilitates immediate release of a therapeutic amount of said anesthetic agent from said anesthetic composition when said apparatus is inserted into said vaginal canal thus inducing temporary anesthesia in the cervical region of said female.

2. The apparatus of claim 1, wherein said pharmaceutically acceptable inert material comprises ethylene-vinyl acetate copolymer, polyethylene, polypropylene, polyurethane, polyvinylchloride, cellulose derivatives, thermoplastic rubber, thermoplastic elastomer, or polydimethylsiloxane.

3. The apparatus of claim 1, wherein said anesthetic composition comprises approximately 60% by weight said anesthetic agent and approximately 40% by weight said excipient.

4. The apparatus of claim 1, wherein said anesthetic agent comprises bupivacaine, ropivacaine, dibucaine, procaine, chloroprocaine, prilocaine, mepivacaine, etidocaine, tetracaine, lidocaine, benzocaine, or a mixture thereof, and said anesthetic is in a free base form, an acid addition salt form, or a mixture thereof.

5. The apparatus of claim 1, wherein said excipient comprises a saturated polyglycolyzed glyceride, a block copolymer surfactant, an emulsifier, glyceryl monolaurate, silicone, microcrystalline cellulose, hydroxyethylcellulose, ethylcellulose, hydroxypropyl methylcellulose, polymethylmethacrylate, polyvinylpyrollidone, or a mixture thereof.

6. The apparatus of claim 1, wherein said at least one depression comprises at least one notch on said exterior surface of said ring.

7. The apparatus of claim 6, wherein said exterior surface of said ring comprises an upper surface, a lower surface, an inner surface and an outer surface, and said at least one notch comprises a plurality of notches on said outer surface.

8. The apparatus of claim 1, wherein said at least one depression comprises at least one channel on said exterior surface of said ring.

9. The apparatus of claim 8, wherein said exterior surface of said ring comprises an upper surface, a lower surface, an inner surface and an outer surface, and said at least one channel is located on said upper surface.

10. The apparatus of claim 8, wherein said exterior surface of said ring comprises an upper surface, a lower surface, an inner surface and an outer surface, and said at least one channel is located on said lower surface.

11. The apparatus of claim 8, wherein said exterior surface of said ring comprises an upper surface, a lower surface, an inner surface and an outer surface, and said at least one channel comprises a first channel located on said upper surface, and a second channel located on said lower surface.

12. The apparatus of claim 8, wherein said exterior surface of said ring comprises an upper surface, a lower surface, an inner surface and an outer surface, and said at least one channel is located on said outer surface.

13. The apparatus of claim 1, wherein said at least one depression comprises at least one bore through said ring.

14. The apparatus of claim 13, wherein said exterior surface of said ring comprises an upper surface, a lower surface, an inner surface and an outer surface, and said at least one bore comprises a plurality of bores through said ring from said upper surface to said lower surface.

15. An apparatus for locally delivering and immediately releasing an anesthetic agent to the cervical region of a female to anesthetize said cervical region, said apparatus comprising:
   (a) a ring having an exterior surface, said exterior surface comprising an inner surface, an outer surface, a lower surface, an upper surface, and a channel on said outer surface, said channel adapted to receive a predetermined amount of an anesthetic composition, wherein said ring is comprised of a pharmaceutically acceptable inert material, and has a sufficient size such that said ring can be inserted into the vaginal canal of said female and retained therein temporarily; and,
   (b) an anesthetic composition located within said channel, wherein said anesthetic composition comprises said anesthetic agent and an excipient which facilitates immediate release of a therapeutic amount of said anesthetic agent from said anesthetic composition when said apparatus is inserted into said vaginal canal thus inducing temporary anesthesia in the cervical region of said female.

16. The apparatus of claim 15, wherein said pharmaceutically acceptable material comprises ethylene-vinyl acetate copolymer, polyethylene, polypropylene, polyurethane, polyvinylchloride, cellulose derivatives, thermoplastic rubber, thermoplastic elastomer, or polydimethylsiloxane.

17. The apparatus of claim 16, wherein said anesthetic composition comprises about 60 % by weight said anesthetic agent, and about 40% by weight said excipient.

18. The apparatus of claim 17, wherein said excipient comprises a saturated polyglycolyzed glyceride, a block copolymer surfactant, an emulsifier, glyceryl monolaurate, silicone, or a mixture thereof.

19. The apparatus of claim 18, wherein said anesthetic agent comprises bupivacaine, ropivacaine, dibucaine, procaine, chloroprocaine, prilocaine, mepivacaine, etidocaine, tetracaine, lidocaine, benzocaine, or a mixture thereof, and said anesthetic agent is in a free base form, an acid addition salt form, or a mixture thereof.

20. The apparatus of claim 19, wherein said anesthetic composition comprises about 60% by weight lidocaine and about 40% by weight saturated polyglycolyzed glyceride.

21. The apparatus of claim 19, wherein said anesthetic composition comprises about 60% by weight lidocaine and about 40% by weight block copolymer surfactant.

22. An apparatus for locally delivering and immediately releasing lidocaine to the cervical region of a female in order to anesthetize said cervical region; said apparatus comprising:
   (a) a ring having an exterior surface comprising an inner surface, an outer surface, a lower surface, an upper surface, and a channel on said outer surface, said channel adapted to receive a predetermined amount of an anesthetic composition, wherein said ring is comprised of ethylene-vinyl acetate copolymer, and has a sufficient size such that it can be inserted into the vaginal canal of said female and retained therein temporarily; and, (b) an anesthetic composition located within said channel, wherein said anesthetic composition comprises about 60% by weight lidocaine and about 40% by weight an excipient which facilitates immediate release of a therapeutic amount of said lidocaine from said anesthetic composition when said apparatus is inserted into said vaginal canal thus inducing temporary anesthesia in the cervical region of said female.

23. The apparatus of claim 22, wherein the excipient comprises a saturated polyglycolyzed glyceride comprising lauroyl macrogolglyceride or stearoyl macrogolglyceride.

24. The apparatus of claim 22, wherein said excipient comprises a block copolymer surfactant.

25. A method for locally delivering and immediately releasing an anesthetic agent to the cervical region of a female in order to anesthetize the cervical region, the method comprising the steps of:
(a) providing a ring having an exterior surface with at least one depression on the exterior surface, said at least one depression adapted to receive a predetermined amount of an anesthetic composition, and an anesthetic composition comprising an anesthetic agent and an excipient which facilitates immediate release of a therapeutic amount of said anesthetic agent from said anesthetic composition when said ring is inserted into the vaginal canal of a female wherein the anesthetic composition is located within the at least one depression, and the ring comprises a pharmaceutically acceptable inert material and has a sufficient size such that it can be inserted into the vaginal canal of the female and retained therein temporarily and,
(b) inserting the ring into the vaginal canal of the female so that the anesthetic agent is immediately released from the anesthetic composition, and induces temporary anesthesia in the cervical region.

26. The method of claim 25, wherein the pharmaceutically acceptable inert material comprises ethylene-vinyl acetate copolymer, polyethylene, polypropylene, polyurethane, polyvinylchloride, cellulose derivatives, thermoplastic rubber, thermoplastic elastomer, or polydimethylsiloxane.

27. The method of claim 25, wherein the anesthetic composition comprises approximately 60% by weight the anesthetic agent and approximately 40% by weight the excipient.

28. The method of claim 25, wherein the anesthetic agent comprises bupivacaine, ropivacaine, dibucaine, procaine, chloroprocaine, prilocaine, mepivacaine, etidocaine, tetracaine, lidocaine, benzocaine, or a mixture thereof, and said anesthetic agent is in a free base form, an acid addition salt form, or a mixture thereof.

29. The method of claim 25, wherein the excipient comprises a saturated polyglycolyzed glyceride, a block copolymer surfactant, an emulsifier, glyceryl monolaurate, silicone, microcrystalline cellulose, hydroxyethylcellulose, ethylcellulose, hydroxypropyl methylcellulose, polymethylmethacrylate, polyvinylpyrollidone, or a mixture thereof.

30. The method of claim 25, wherein the said at least one depression comprises at least one notch on the surface of the ring.

31. The method of claim 30, wherein the exterior surface of the ring comprises an upper surface, a lower surface, an inner surface and an outer surface, and the at least one notch comprises a plurality of notches on the outer surface.

32. The method of claim 25, wherein the at least one depression comprises at least one channel on the surface of the ring.

33. The method of claim 32, wherein the exterior surface of the ring comprises an upper surface, a lower surface, an inner surface and an outer surface, and the at least one channel is located on the upper surface.

34. The method of claim 32, wherein the exterior surface of the ring comprises an upper surface, a lower surface, an inner surface and an outer surface, and the at least one channel is located on the lower surface.

35. The method of claim 32, wherein the exterior surface of the ring comprises an upper surface, a lower surface, an inner surface and an outer surface, and the at least one channel comprises a first channel located on the upper surface, and a second channel located on the lower surface.

36. The method of claim 32, wherein the exterior surface of the ring comprises an upper surface, a lower surface, an inner surface and an outer surface, and the at least one channel is located on the outer surface.

37. The method of claim 25, wherein the at least one depression comprises at least one bore in the ring.

38. The method of claim 37, wherein the exterior surface of the ring comprises an upper surface, a lower surface, an inner surface and an outer surface, and the at least one bore comprises a plurality of bores which pass through the ring from the upper surface to the lower surface.

39. A method for locally delivering and immediately releasing an anesthetic agent to the cervical region of a female to temporarily anesthetize the cervical region, the method comprising the steps of:
(a) providing a ring having an exterior surface comprising an inner surface, an outer surface, a lower surface, an upper surface, and a channel on the outer surface, said channel adapted to receive a predetermined amount of an anesthetic composition wherein the ring comprises ethylene-vinyl acetate copolymer, and has a sufficient size such that it can be inserted into the vaginal canal of the female and be retained therein temporarily;
(b) providing an anesthetic composition located within the channel, wherein the anesthetic composition comprises the anesthetic agent and an excipient which facilitates immediate release of a therapeutic amount of said anesthetic agent from said anesthetic composition when said ring is inserted into the vaginal canal of said female;
(c) inserting the ring into the vaginal canal of the female such that the anesthetic agent is immediately released from the anesthetic composition, and induces temporary anesthesia in the cervical region; and,
(d) removing the ring from the vaginal canal after inducing temporary anesthesia in the cervical region either to or after performance of a gynecological procedure.

40. The method of claim 39, wherein the anesthetic composition comprises about 60% by weight the anesthetic agent, and about 40% by weight the excipient.

41. The method of claim 40, wherein the excipient comprises a saturated polyglycolyzed glyceride, a block copolymer surfactant, an emulsifier, glyceryl monolaurate, silicone, or a mixture thereof.

42. The method of claim 41, wherein the anesthetic agent comprises bupivacaine, ropivacaine, dibucaine, procaine, chloroprocaine, prilocaine, mepivacaine, etidocaine, tetracaine, lidocaine, benzocaine, or a mixture thereof, and the anesthetic agent is in a free base form, an acid addition salt form, or a mixture thereof.

43. The method of claim 42 wherein the anesthetic composition comprises about 60% by weight lidocaine and about 40% by weight saturated polyglycolyzed glyceride.

44. The method of claim 42, wherein the anesthetic composition comprises about 60% by weight lidocaine and about 40% by weight block copolymer surfactant.

45. A method for locally delivering and immediately releasing lidocaine to the cervical region of a female in order to anesthetize the cervical region; the method comprising the steps of:

(a) providing a ring having an exterior surface comprising an inner surface, an outer surface, a lower surface, an upper surface, and a channel on the outer surface, said channel adapted to receive a predetermined amount of an anesthetic composition wherein the ring comprises ethylene-vinyl acetate copolymer and has a sufficient size such that it can be inserted into the vaginal canal of the female and retained therein temporarily;

(b) providing an anesthetic composition located within the channel, wherein the anesthetic composition comprises about 60% by weight lidocaine and about 40% by weight an excipient which immediately releases a therapeutic amount of said lidocaine from said anesthetic composition when said ring is inserted into said vaginal canal;

(c) inserting the ring into the vaginal canal of the female so that the anesthetic agent is immediately released from the anesthetic composition and induces temporary anesthesia in the cervical region; and, (d) removing the ring from the vaginal canal after induction of temporary anesthesia in the cervical region either prior to or after performance of a gynecological procedure.

46. The method of claim 45, wherein the excipient comprises a saturated polygylcolyzed glyceride comprising lauroyl macrogoglyceride or stearoyl macrogoglyceride.

47. The method of claim 45, wherein the excipient comprises a block copolymer surfactant.

* * * * *